(12) United States Patent
Hartwell

(10) Patent No.: US 12,127,918 B2
(45) Date of Patent: *Oct. 29, 2024

(54) COLLAPSIBLE STRUCTURE AND METHOD OF USE

(71) Applicant: Smith & Nephew PLC, Watford (GB)

(72) Inventor: Edward Yerbury Hartwell, Hull (GB)

(73) Assignee: Smith & Nephew PLC, Watford (GB)

( * ) Notice: Subject to any disclaimer, the term of this patent is extended or adjusted under 35 U.S.C. 154(b) by 21 days.

This patent is subject to a terminal disclaimer.

(21) Appl. No.: 17/726,058

(22) Filed: Apr. 21, 2022

(65) Prior Publication Data

US 2022/0241488 A1 Aug. 4, 2022

Related U.S. Application Data

(63) Continuation of application No. 16/622,244, filed as application No. PCT/EP2018/065398 on Jun. 11, 2018, now Pat. No. 11,324,876.

(60) Provisional application No. 62/518,718, filed on Jun. 13, 2017.

(51) Int. Cl.
    *A61F 13/05* (2024.01)
    *A61F 13/00* (2024.01)
    *A61M 1/00* (2006.01)

(52) U.S. Cl.
    CPC .... *A61F 13/05* (2024.01); *A61F 2013/00174* (2013.01); *A61F 2013/00536* (2013.01); *A61M 1/74* (2021.05); *A61M 1/90* (2021.05)

(58) Field of Classification Search
    CPC .............. A61B 17/083; A61B 17/1227; A61B 2017/00566; A61F 13/00068; A61F 13/0216; A61F 2013/00174; A61F 2013/00536; A61M 1/74; A61M 1/90; A61M 1/915

See application file for complete search history.

(56) References Cited

U.S. PATENT DOCUMENTS

| 3,194,239 A | 7/1965 | Sullivan et al. |
| 3,789,851 A | 2/1974 | LeVeen |
| 4,467,805 A | 8/1984 | Fukuda |
| 4,608,041 A | 8/1986 | Nielsen |

(Continued)

FOREIGN PATENT DOCUMENTS

| AU | 2012261793 B2 | 11/2014 |
| AU | 2013206230 B2 | 5/2016 |

(Continued)

OTHER PUBLICATIONS

"Definition of 3D Printer," American Heritage Dictionary of the English Language, Fifth Edition, accessed on Feb. 22, 2018 from URL: https://www.thefreedictionary.com, 2016, 1 page.

(Continued)

*Primary Examiner* — Leslie A Lopez
*Assistant Examiner* — Jihad Dakkak
(74) *Attorney, Agent, or Firm* — Knobbe, Martens, Olson & Bear, LLP

(57) ABSTRACT

A collapsible, clamping and/or steerable apparatus in conjunction with negative pressure system and methods for using such an apparatus are described. Preferred embodiments of the invention have lengths and bent and/or increase their curvatures along their lengths, by preferentially contracting and transforming upon negative pressure.

22 Claims, 37 Drawing Sheets

(56) References Cited

U.S. PATENT DOCUMENTS

| | | |
|---|---|---|
| 4,699,134 A | 10/1987 | Samuelsen |
| 4,815,468 A | 3/1989 | Annand |
| 5,176,663 A | 1/1993 | Svedman et al. |
| 5,264,218 A | 11/1993 | Rogozinski |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 6,176,868 B1 | 1/2001 | Detour |
| 6,503,208 B1 | 1/2003 | Skovlund |
| 6,548,727 B1 | 4/2003 | Swenson |
| 6,566,575 B1 | 5/2003 | Stickels et al. |
| 6,685,681 B2 | 2/2004 | Lockwood et al. |
| 6,770,794 B2 | 8/2004 | Fleischmann |
| 6,787,682 B2 | 9/2004 | Gilman |
| 6,977,323 B1 | 12/2005 | Swenson |
| 7,004,915 B2 | 2/2006 | Boynton et al. |
| 7,144,390 B1 | 12/2006 | Hannigan et al. |
| 7,315,183 B2 | 1/2008 | Hinterscher |
| 7,351,250 B2 | 4/2008 | Zamierowski |
| 7,361,184 B2 | 4/2008 | Joshi |
| 7,438,705 B2 | 10/2008 | Karpowicz et al. |
| 7,494,482 B2 | 2/2009 | Orgill et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,683,667 B2 | 3/2010 | Kim |
| 7,700,819 B2 | 4/2010 | Ambrosio et al. |
| 7,754,937 B2 | 7/2010 | Boehringer et al. |
| 7,779,625 B2 | 8/2010 | Joshi et al. |
| 7,815,616 B2 | 10/2010 | Boehringer et al. |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 8,030,534 B2 | 10/2011 | Radl et al. |
| 8,057,447 B2 | 11/2011 | Olson et al. |
| 8,062,331 B2 | 11/2011 | Zamierowski |
| 8,067,662 B2 | 11/2011 | Aali et al. |
| 8,070,773 B2 | 12/2011 | Zamierowski |
| 8,114,126 B2 | 2/2012 | Heaton et al. |
| 8,123,781 B2 | 2/2012 | Zamierowski |
| 8,142,419 B2 | 3/2012 | Heaton et al. |
| 8,172,816 B2 | 5/2012 | Kazala, Jr. et al. |
| 8,187,237 B2 | 5/2012 | Seegert |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,590 B2 | 8/2012 | Hu et al. |
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,376,972 B2 | 2/2013 | Fleischmann |
| 8,430,867 B2 | 4/2013 | Robinson et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,776 B2 | 8/2013 | Ebner |
| 8,608,776 B2 | 12/2013 | Coward et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,721,629 B2 | 5/2014 | Hardman et al. |
| 8,746,662 B2 | 6/2014 | Poppe |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,821,535 B2 | 9/2014 | Greener |
| 8,945,030 B2 | 2/2015 | Weston |
| 9,044,579 B2 | 6/2015 | Blott et al. |
| 9,061,095 B2 | 6/2015 | Adie et al. |
| 9,180,231 B2 | 11/2015 | Greener |
| 9,408,755 B2 | 8/2016 | Larsson |
| 9,421,132 B2 | 8/2016 | Dunn |
| 9,655,807 B2 | 5/2017 | Locke et al. |
| 9,849,023 B2 | 12/2017 | Hall et al. |
| 10,143,485 B2 | 12/2018 | Locke et al. |
| 11,375,923 B2 * | 7/2022 | Hunt ..................... G01V 3/088 |
| 11,439,539 B2 * | 9/2022 | Dunn .................... A61M 1/913 |
| 2001/0034499 A1 | 10/2001 | Sessions et al. |
| 2002/0077661 A1 | 6/2002 | Saadat |
| 2002/0161346 A1 | 10/2002 | Lockwood et al. |
| 2004/0162512 A1 | 8/2004 | Liedtke et al. |
| 2004/0267312 A1 | 12/2004 | Kanner et al. |
| 2005/0142331 A1 | 6/2005 | Anderson et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0069357 A1 | 3/2006 | Marasco |
| 2006/0155260 A1 | 7/2006 | Blott et al. |
| 2006/0217795 A1 | 9/2006 | Besselink et al. |
| 2006/0271018 A1 | 11/2006 | Korf |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |
| 2008/0041401 A1 | 2/2008 | Casola et al. |
| 2008/0108977 A1 | 5/2008 | Heaton et al. |
| 2008/0243096 A1 | 10/2008 | Svedman |
| 2008/0275409 A1 | 11/2008 | Kane et al. |
| 2008/0306456 A1 | 12/2008 | Riesinger |
| 2009/0005716 A1 | 1/2009 | Abuzaina et al. |
| 2009/0099519 A1 | 4/2009 | Kaplan |
| 2009/0105670 A1 | 4/2009 | Bentley et al. |
| 2009/0204423 A1 | 8/2009 | DeGheest et al. |
| 2009/0312685 A1 | 12/2009 | Olsen et al. |
| 2010/0022990 A1 | 1/2010 | Karpowicz et al. |
| 2010/0047324 A1 | 2/2010 | Fritz et al. |
| 2010/0081983 A1 | 4/2010 | Zocher et al. |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0224631 A1 | 9/2011 | Simmons et al. |

(56) References Cited

U.S. PATENT DOCUMENTS

| | | | |
|---|---|---|---|
| 2011/0224632 A1 | 9/2011 | Zimnitsky et al. | |
| 2011/0224634 A1 | 9/2011 | Locke et al. | |
| 2011/0264138 A1 | 10/2011 | Avelar et al. | |
| 2011/0270301 A1 | 11/2011 | Cornet et al. | |
| 2011/0305736 A1 | 12/2011 | Wieland et al. | |
| 2012/0016321 A1 | 1/2012 | Wu et al. | |
| 2012/0029455 A1 | 2/2012 | Perez-Foullerat et al. | |
| 2012/0059412 A1 | 3/2012 | Fleischmann | |
| 2012/0130327 A1 | 5/2012 | Marquez Canada | |
| 2012/0136326 A1 | 5/2012 | Croizat et al. | |
| 2012/0136328 A1 | 5/2012 | Johannison et al. | |
| 2012/0143113 A1 | 6/2012 | Robinson et al. | |
| 2012/0172926 A1 | 7/2012 | Hotter | |
| 2012/0191132 A1 | 7/2012 | Sargeant | |
| 2012/0209226 A1 | 8/2012 | Simmons et al. | |
| 2012/0209227 A1* | 8/2012 | Dunn | A61M 1/84 604/319 |
| 2012/0253302 A1 | 10/2012 | Corley | |
| 2013/0023842 A1 | 1/2013 | Song | |
| 2013/0150813 A1 | 6/2013 | Gordon et al. | |
| 2013/0190705 A1 | 7/2013 | Vess et al. | |
| 2013/0197457 A1 | 8/2013 | Kazala, Jr. et al. | |
| 2013/0204213 A1 | 8/2013 | Heagle et al. | |
| 2013/0245527 A1 | 9/2013 | Croizat et al. | |
| 2013/0325142 A1 | 12/2013 | Hunter et al. | |
| 2013/0331757 A1 | 12/2013 | Belson | |
| 2014/0094730 A1 | 4/2014 | Greener et al. | |
| 2014/0163415 A1 | 6/2014 | Zaiken et al. | |
| 2014/0180225 A1* | 6/2014 | Dunn | A61F 13/05 604/319 |
| 2014/0249495 A1 | 9/2014 | Mumby et al. | |
| 2015/0065968 A1 | 3/2015 | Sealy et al. | |
| 2015/0112311 A1 | 4/2015 | Hammond et al. | |
| 2015/0119837 A1 | 4/2015 | Thompson, Jr. et al. | |
| 2015/0157758 A1 | 6/2015 | Blucher et al. | |
| 2015/0190288 A1* | 7/2015 | Dunn | A61F 13/00068 604/319 |
| 2015/0196431 A1 | 7/2015 | Dunn et al. | |
| 2015/0216732 A1 | 8/2015 | Hartwell et al. | |
| 2015/0320602 A1 | 11/2015 | Locke et al. | |
| 2015/0374561 A1 | 12/2015 | Hubbard, Jr. et al. | |
| 2016/0144085 A1 | 5/2016 | Melin et al. | |
| 2016/0184496 A1 | 6/2016 | Jaecklein et al. | |
| 2016/0287765 A1* | 10/2016 | Canner | A61F 13/00995 |
| 2017/0065751 A1 | 3/2017 | Toth | |
| 2017/0281838 A1 | 10/2017 | Dunn | |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2279016 A1 | 2/2011 |
| EP | 2567717 A1 | 3/2013 |
| GB | 2389794 A | 12/2003 |
| GB | 2423019 A | 8/2006 |
| GB | 2489947 A | 10/2012 |
| GB | 2496310 A | 5/2013 |
| JP | S6257560 A | 3/1987 |
| JP | 2012105840 A | 6/2012 |
| RU | 62504 U1 | 4/2007 |
| SU | 1818103 A1 | 5/1993 |
| WO | WO-0185248 A1 | 11/2001 |
| WO | WO-0189392 A2 | 11/2001 |
| WO | WO-0205737 A1 | 1/2002 |
| WO | WO-03003948 A1 | 1/2003 |
| WO | WO-03049598 A2 | 6/2003 |
| WO | WO-2005046761 A1 | 5/2005 |
| WO | WO-2005105174 A1 | 11/2005 |
| WO | WO-2006046060 A2 | 5/2006 |
| WO | WO-2008027449 A2 | 3/2008 |
| WO | WO-2008064502 A1 | 6/2008 |
| WO | WO-2008104609 A1 | 9/2008 |
| WO | WO-2009112062 A1 | 9/2009 |
| WO | WO-2010033725 A2 | 3/2010 |
| WO | WO-2010097570 A1 | 9/2010 |
| WO | WO-2011023384 A1 | 3/2011 |
| WO | WO-2012082716 A2 | 6/2012 |
| WO | WO-2012082876 A1 | 6/2012 |
| WO | WO-2012136707 A1 | 10/2012 |
| WO | WO-2012142473 A1 | 10/2012 |
| WO | WO-2013012381 A1 | 1/2013 |
| WO | WO-2013043258 A1 | 3/2013 |
| WO | WO-2013071243 A2 | 5/2013 |
| WO | WO-2013076450 A1 | 5/2013 |
| WO | WO-2013079947 A1 | 6/2013 |
| WO | WO-2013175309 A1 | 11/2013 |
| WO | WO-2013175310 A2 | 11/2013 |
| WO | WO-2014013348 A2 | 1/2014 |
| WO | WO-2014140578 A1 | 9/2014 |
| WO | WO-2014158526 A1 | 10/2014 |
| WO | WO-2014165275 A1 | 10/2014 |
| WO | WO-2014178945 A1 | 11/2014 |
| WO | WO-2014194786 A1 | 12/2014 |
| WO | WO-2015008054 A1 | 1/2015 |
| WO | WO-2015061352 A2 | 4/2015 |
| WO | WO-2015109359 A1 | 7/2015 |
| WO | WO-2015110409 A1 | 7/2015 |
| WO | WO-2015110410 A1 | 7/2015 |
| WO | WO-2015169637 A1 | 11/2015 |
| WO | WO-2015193257 A1 | 12/2015 |
| WO | WO-2016018448 A1 | 2/2016 |
| WO | WO-2016176513 A1 | 11/2016 |
| WO | WO-2016179245 A1 | 11/2016 |
| WO | WO-2017106576 A1 | 6/2017 |
| WO | WO-2018038665 A1 | 3/2018 |
| WO | WO-2018041805 A1 | 3/2018 |
| WO | WO-2018044944 A1 | 3/2018 |
| WO | WO-2018044949 A1 | 3/2018 |
| WO | WO-2018085457 A1 | 5/2018 |
| WO | WO-2018140386 A2 | 8/2018 |
| WO | WO-2018237206 A2 | 12/2018 |

OTHER PUBLICATIONS

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

International Preliminary Report on Patentability for Application No. PCT/EP2018/065398, mailed on Dec. 26, 2019, 9 pages.

International Search Report and Written Opinion for Application No. PCT/EP2018/065398, mailed on Jul. 26, 2018, 12 pages.

Kapischke M., et al., "Self-Fixating Mesh for the Lichtenstein Procedure—a Prestudy," Langenbeck's Arch Surg, 2010, vol. 395, pp. 317-322.

* cited by examiner

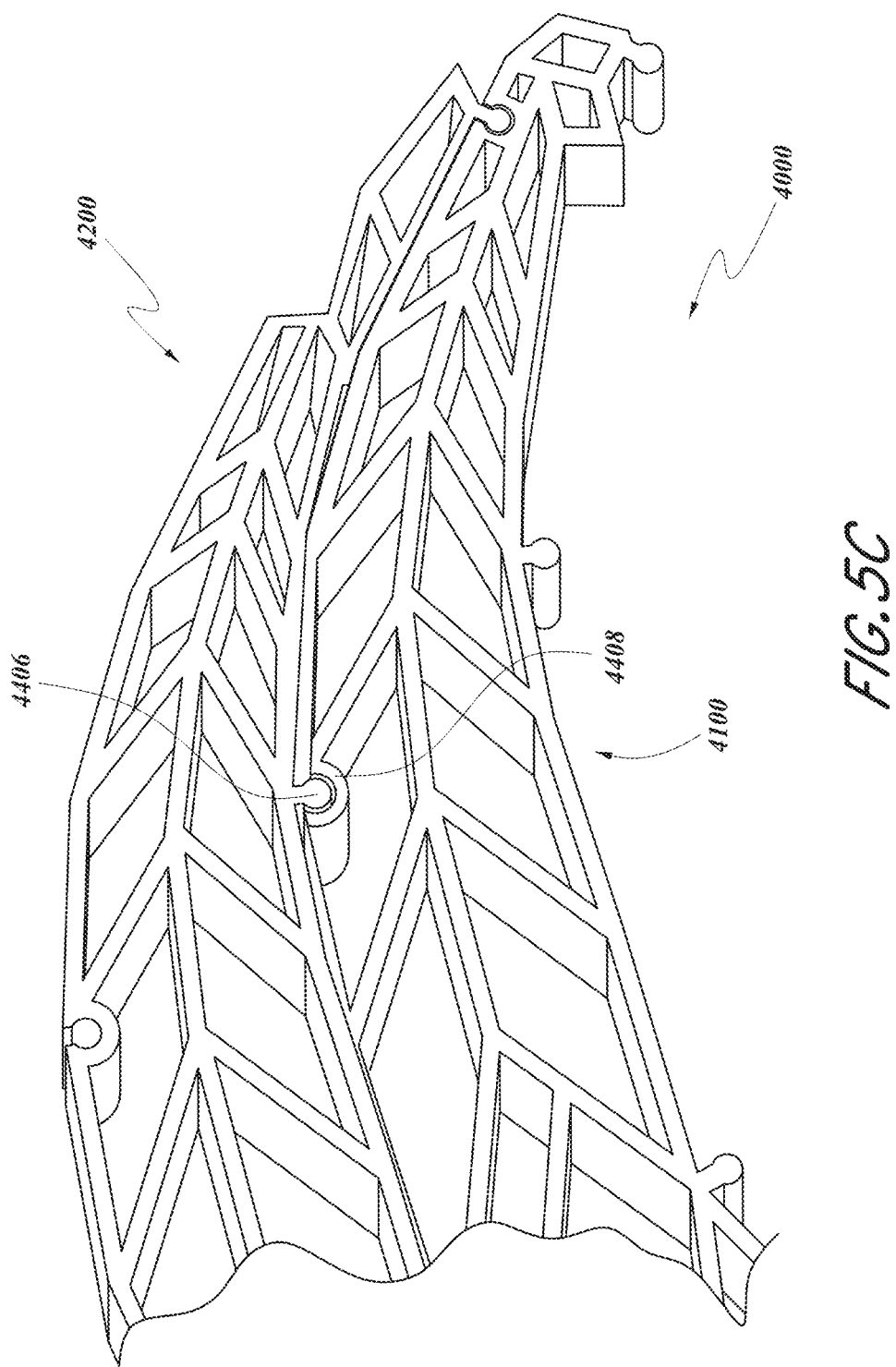

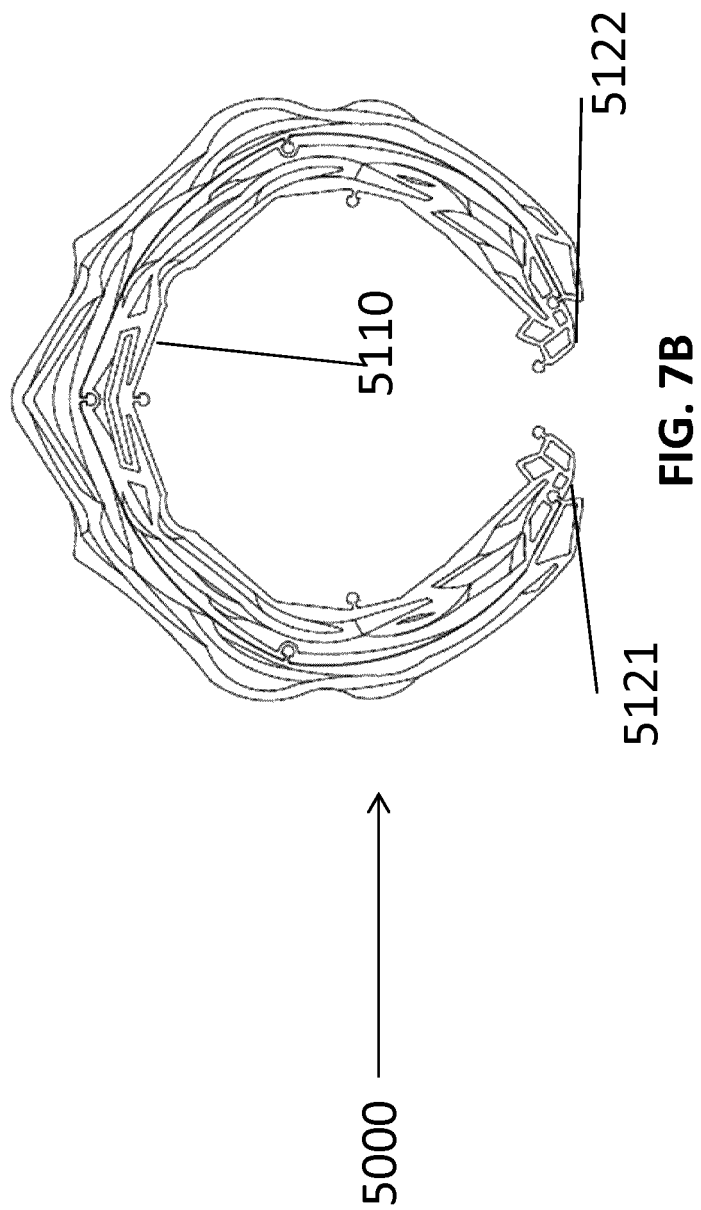

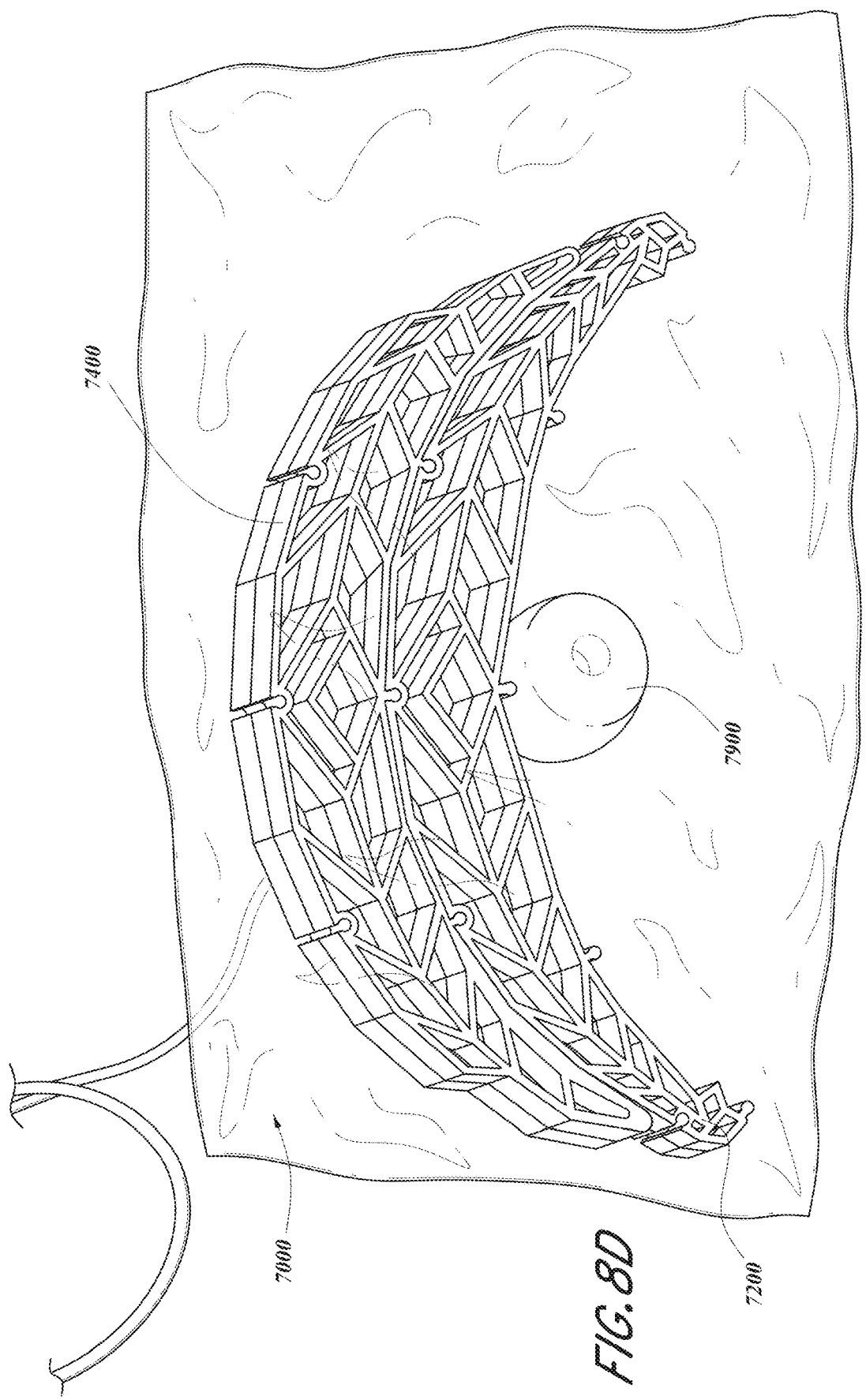

COLLAPSIBLE STRUCTURE AND METHOD OF USE

CROSS-REFERENCE TO RELATED APPLICATIONS

This application is a continuation application of U.S. application Ser. No. 16/622,244, filed Dec. 12, 2019, which is a U.S. national stage application of International Patent Application No. PCT/EP2018/065398, filed Jun. 11, 2018, which claims priority to U.S. Provisional Application No. 62/518,718 filed on Jun. 13, 2017, which is incorporated by reference in its entirety.

BACKGROUND

Field of Use

This application describes embodiments of apparatuses, methods, and systems for the use of a collapsible, clamping and/or steerable structure in conjunction with negative pressure.

Description of the Related Art

Negative pressure, or partial vacuum, is widely used in many areas, such as in laboratories, medical facilities, factories, or even in household. The usefulness of negative pressure comes from a variety of characteristics. For example, negative pressure provides chemical inertness, promotes evaporation and sublimation, and produces suction powers. Also, some structure or materials may change its shape or structure under negative pressure. For example, a porous sponge may collapse under negative pressure. Even though a normal sponge will only shrink in all dimensions, development of a structure which changes shape into a more desirable shape under negative pressure may be possible.

SUMMARY

Embodiments of the present invention relate to apparatus, methods, and systems for the use in conjunction with the administration of negative pressure. Specifically, the apparatus of certain embodiments may be designed to adjust its curvature along its length under negative pressure. Such steerable structure would be useful in many ways and can be applied to various curved objects under various degrees of negative pressure. Or, such steerable structure may be also used as a clamping device under negative pressure, to grip and/or clamp around particular objects. By reversibly changing structure, a clamping device may releasably hold multiple articles together, and a steerable structure may grab one or multiple articles together by changing its curvature. However, it will be understood by one of skill of art that application of the apparatuses, methods, and systems described herein this specification may be in any manner in relation to negative pressure, and are not limited to the clamping or any other particular use.

In some embodiments, a collapsible structure may be provided to collapse under negative pressure. The collapsible structure may comprise a plurality of cells, wherein the cells are shaped to preferentially collapse to form one or more desired shapes. For example, the cells may be shaped to cause the structure to collapse from an initial shape, such as a straight shape or a crescent shape in which opposite ends of the structure are relatively further apart, to a collapsed shape, such as a relatively more curved shape or a circular shape wherein the ends of the structure are relatively closer together. Compound shapes may also be provided by combining multiple collapsible structures together in different orientations. The collapsible structure may be enclosed within a cover member to form an enclosed, airtight space. Application of negative pressure to the enclosed space can cause the collapsible structure to collapse from the initial shape to the collapsed shape.

In certain embodiments, an apparatus for use with negative pressure is provided, the apparatus comprises a clamping structure having a first end, a second end, a length extending from the first end and the second end, a width transverse to the length extending along a central transverse axis of the clamping structure, and a height transverse to the length and the width, wherein the length and width are greater than the height. The clamping structure comprises a first side and a second side extending the length of the clamping structure from the first end to the second end in parallel or semi-parallel fashion. The first side is opposite the second side.

A plurality of elongate strips may extend the length of the clamping structure from the first end to the second end. The plurality of elongate strips may comprise two outermost elongate strips defining the first side and the second side.

A plurality of intervening members may connect the plurality of elongate strips. The plurality of intervening members may be configured to pivot relative to the strips to allow the plurality of elongate strips to collapse relative to one another.

A plurality of cells may be provided side-by-side in the clamping structure in a horizontal plane parallel to the length and width of the clamping structure. Each cell may be defined by a plurality of walls formed by either the elongate strips or the intervening members. Each cell may have a top end and a bottom end with an opening extending through the top and bottom ends. The plurality of elongate strips may be configured to increase curvature upon collapse of the plurality of cells.

In certain embodiments, the first side of the clamping structure may be a concave side and the second side of the clamping structure may be a convex side. The concave side is curved or bent concavely with respect to the clamping structure. The convex side is curved or bent convexly with respect to the clamping structure. The first side and the second side may taper toward the first and second end. The length of the clamping structure is greater than the width of the clamping structure. The clamping structure may be symmetrical about the central transverse axis. The clamping structure may be at least partially crescent-shaped.

In certain embodiments, the plurality of elongate strips further comprises at least one elongate strip positioned between the first side and the second side. Each of the elongate strips may be arranged in parallel or semi-parallel fashion. In some embodiments, at least some of the cells are diamond-shaped. At least some of the diamond-shaped cells may be subdivided from larger diamond-shaped cells. At least some of the cells may parallelpiped-shaped. The lengths of the cells along an elongate strip may be progressively shorter toward the first end and the second end.

In certain embodiments, the clamping structure comprises one or more detachable segments. The one or more detachable segments may comprise attachment elements. The clamping structure may further comprise an inner segment at least partially surrounded by one or more detachable segments. The inner segment may comprise receiving elements configured to receive attachment elements of the one or more detachable segments.

In certain embodiments, an apparatus for use with negative pressure comprises a first clamping structure and a second clamping structure. The second clamping structure is positioned over the first clamping structure. The second clamping structure may be attached to a top of the first clamping structure. In certain embodiments, the second clamping structure comprises receiving elements configured to receive attachment elements of the first clamping structure.

In certain embodiments, the apparatus for use with negative pressure further comprises a source or negative pressure, a drape and/or a port. The port is configured to transmit negative pressure through a drape placed over the structure.

In certain embodiments, a method of grabbing one or more objects comprises providing the clamping structure and applying the clamping structure on the surface of one or more objects. In some embodiments, the first side of the clamping structure is a concave side and the second side of the clamping structure is a convex side and the concave side is curved or bent concavely with respect to the clamping structure, and the convex side is curved or bent convexly with respect to the clamping structure. The one or more objects may comprise a curve along its surface and the clamping structure is applied on the surface of one or more object so that the concave side is aligned along the curve of the one or more objects. In certain embodiments, the method further comprises covering the clamping structure with a drape sealed to the surface of one or more objects surrounding one or more object and applying negative pressure through the drape to the structure via a source of negative pressure, wherein the application of negative pressure causes the stabilizing structure to horizontally collapse.

Other embodiments of an apparatus for use with negative pressure, devices and associated apparatuses are described below.

BRIEF DESCRIPTION OF THE DRAWINGS

FIGS. 5A-I illustrate embodiments of a clamping structure having a detachable segment.

FIGS. 7A-D illustrate embodiments of a clamping structure having a detachable segment in a natural state and a collapsed state.

FIGS. 8D-8E are photographs of an embodiment of a stacked clamping structure.

DETAILED DESCRIPTION

Figure 1:
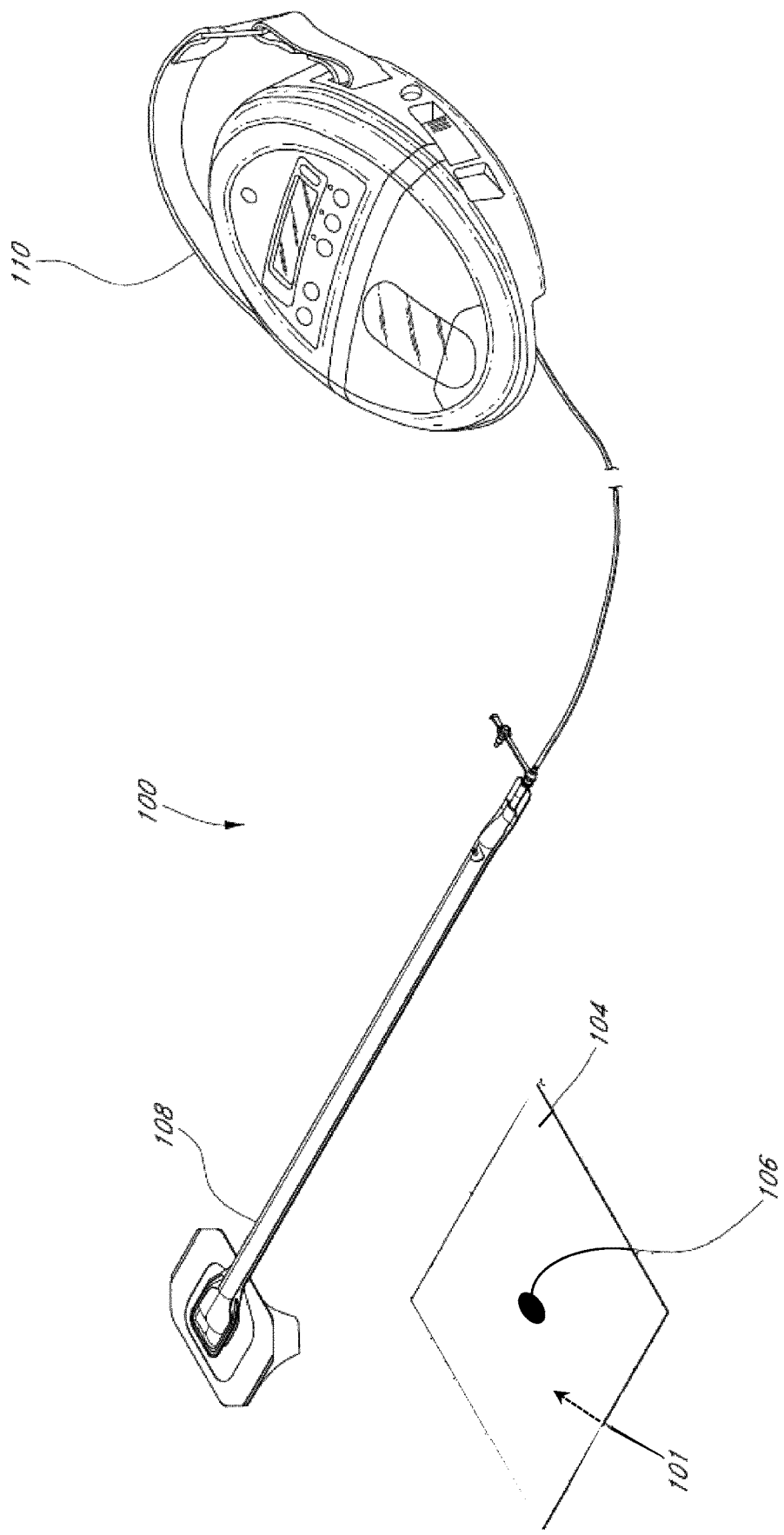
FIG. 1 illustrates an embodiment of a negative pressure treatment system.

Embodiments disclosed in this section or elsewhere in this specification relate to apparatuses and methods to be used with reduced pressure, including clamping structures that collapse and transform with reduced pressure.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −10 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments, a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas.

It will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 time, 10 times, 12 times or greater than the height of the face.

The terms "horizontal," "vertical," "longitudinal," and "lateral" may be used to describe the clamping structures described throughout this specification. When describing these structures or devices, these terms should not be construed to require that the structures or devices necessarily be placed in a certain orientation, though in certain embodiments, it may be preferable to do so.

FIG. 1 illustrates an embodiment of a negative pressure system 100 having a site 101 where negative pressure is applied. A single drape 104 or multiple drapes may be placed over the site 101 to create a fluid-tight seal. Under the drape 104, the system may include a collapsible structure which is not shown in FIG. 1. The collapsible structure may include porous materials such as foam, and in some embodiments, one or more clamping structures described in further detail in this section or elsewhere in this specification. An aperture 106 may be made through the drape 104 which can be manually made or preformed into the drape 104 so as to provide a fluidic connection from the site 101 to a source of negative pressure such as a pump 110. Preferably, the fluidic connection between the aperture 106 and the pump 110 is made via a conduit 108. Of course, in some embodiments, the drape 104 may not necessarily comprise an aperture 106, and the fluidic connection to the pump 110 may be made by placing the conduit 108 below the drape.

Figure 2A:
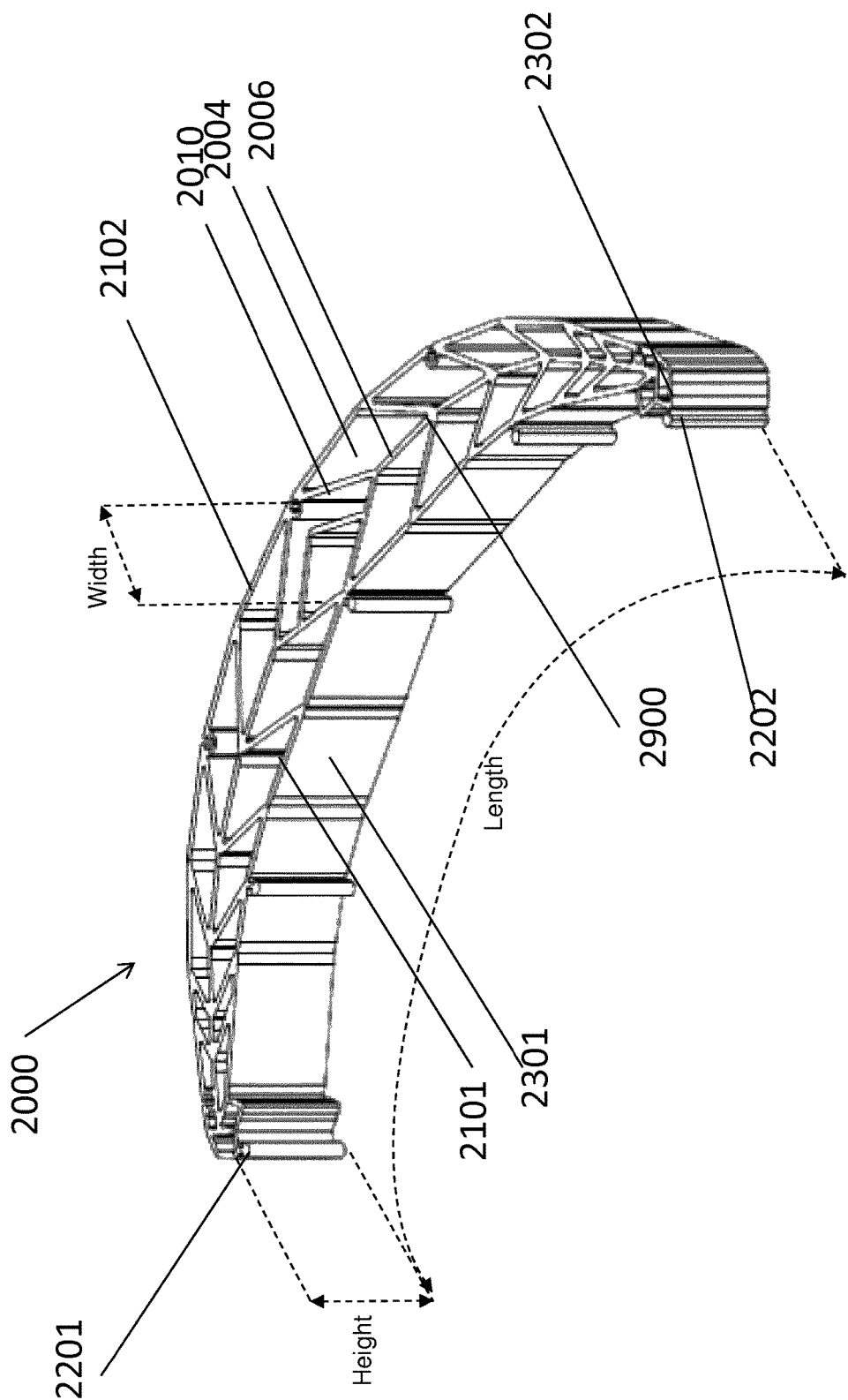
FIG. 2A illustrates a perspective of an embodiment of a clamping structure.
Figure 2B:
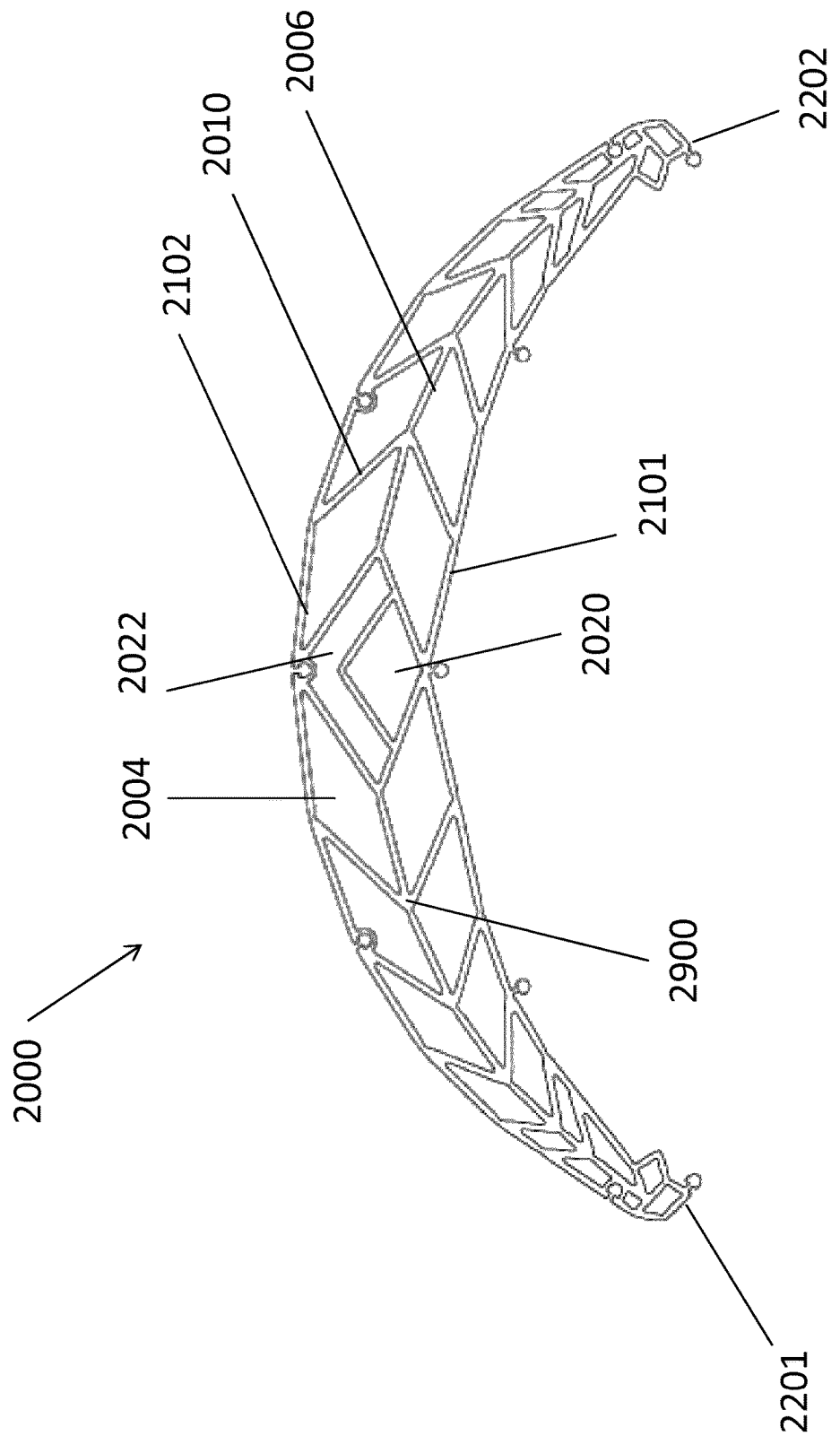
FIG. 2B illustrates a top view of an embodiment of a clamping structure
Figure 2C:
FIG. 2C is a photograph of an embodiment of a clamping structure.

FIGS. 2A-C: Clamping Structure and its Elements

Development of a structure which changes shape into a more desirable shape under negative pressure may be possible. For instance, a structure having length may be designed to adjust its curvature along its length under negative pressure. Such steerable structure would be useful in many ways and can be applied to various curved objects under various degrees of negative pressure. For example, such steerable structures may be used for steerable endoscopes, stents or catheters. Such steerable structures may be also used for splints to stabilize limbs, where the curvature and shape of the splint can be adjusted by negative pressure. Further, compound shapes may also be provided by combining multiple collapsible structures together in different orientations. Or, such steerable structure may be also used as a clamping device under negative pressure, to grip and/or clamp around particular objects. By reversibly changing structure, a clamping device may releasably hold multiple articles together, and a steerable structure may grab one or multiple articles together by changing its curvature. Such clamping devices may be utilized as powered forceps or tweezers, particularly where no electrical isolation is required.

FIGS. 2A-B illustrate an embodiment of a clamping structure 2000 comprising a plurality of elongate strips 2006 arranged in parallel or semi-parallel fashion. FIG. 2C is a photograph of an embodiment of a clamping structure 2000. In embodiments, the elongate strips may also be arranged in a non-parallel fashion. The various cells within this clamping structure 2000 may have a variety of shapes and sizes. As will be described in greater detail below, the length and shape of the elongate strips 2006, intervening members 2010, and cells 2004 may be designed so as to facilitate collapse and thus greater transformation of the clamping structure. In certain embodiments, the junctions 2900 between the elongate strips and intervening members may be thinned to better facilitate rotation and thus clamping of the clamping structures. In some embodiments, the clamping structure is tearable, such that the structure may be shaped into any desired size or shape. As described elsewhere in the specification, tears may be completed at the intersections between intervening members and elongate strips or at any suitable location along the elongate strip or intervening member.

All clamping structures described herein this section or elsewhere in the specification may be fashioned to be any size. However, to better accommodate the needs of the clinical environment, in certain embodiments, the clamping structures described herein may be provided in a pack of two sizes, one smaller clamping structure and one larger clamping structure about 1.25 times as larger, about 1.5 times as large, about 1.75 times as large, about 2 times as larger, about 2.5 times as larger, about 3 times as large, about 4 times as large, about 5 times as large, or more than about 5 times as large. In some embodiments, the pack may comprise more than two sizes, such as three sizes, four sizes, five sizes, or more than five sizes. The clamping structures within the pack may be of a variety of sizes in relation to one another such as the ratios described above.

In certain embodiments, the clamping structure 2000 can collapse in any manner described in this section or elsewhere in this specification with or without the application of negative pressure. For example, the clamping structure may collapse significantly more in one plane than in another plane upon application of negative pressure. In some embodiments, a particular row of cells may collapse in a first direction, while another row may collapse in the same or an opposing direction. In certain embodiments, the clamping structure may collapse along the width of the clamping structure while remaining relatively rigid along the length and the height of the clamping structure. In certain embodiments, the clamping structure may also transform its overall shape while collapsing.

The clamping structure may be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam.

Returning to FIG. 2A, clamping structure 2000 may have a concave side 2101 and a convex side 2102, each extending the length of the clamping structure from a first end 2201 to a second end 2202 and the convex side is opposing the concave side. The concave side 2101 and the convex side 2102 are defined by two outermost elongate strips. In some embodiments, as shown by FIGS. 2A-C, each of the concave side and the convex side may have a partial-elliptical shape. In certain embodiments, the concave side and the convex side are bent or curved in same direction so that they are aligned in semi-parallel fashion. For example, as shown by FIGS. 2A-C, the concave side may be bent or curved concavely with respect to the clamping structure and the convex side may be bent or curved convexly with respect to the clamping structure. In other embodiments, the concave side may be straight while the convex side is curved or bent. In other embodiments, the concave side and the convex side may be bent or curved in opposite direction. In some embodiments, such as in FIGS. 2A-C, the concave side and the convex side may taper toward the first and the second end. In some embodiments, the clamping structure may be at least partially crescent-shaped. In other embodiments, the clamping structure may be at least partially half-elliptical-shaped. In some embodiments, the clamping structure may be symmetrical about the central transverse axis.

The clamping structure 2000 further may comprise a concave side wall 2301 defined by the concave side 2101 along the height of the clamping structure, and a convex side wall 2302 defined by the convex side 2102 along the height of the clamping structure. In some embodiments, both of concave side wall and the convex side wall are parallel with the height and make up the right angle with regard to the horizontal plane. In other embodiments, either of the concave side wall and the convex side wall will be tilted with regard to the height. In some embodiments, the concave side wall and the convex side wall are straight along the height. In other embodiments, the concave side wall and the convex side wall may be curved along the height, so that the clamping structure can be more suitably applied to a contoured object. For example, when the concave side wall of the clamping structure is configured to be applied to a spherical object, the side wall may be designed to be concave along the height as well, so that it better fits with the spherical object.

As described above, the clamping structure 2000 may comprise a plurality of cells 2004 provided side-by-side, each cell defined by one or more walls, each cell having a top end and a bottom end with an opening extending through the top and bottom ends. As with the other clamping structures described herein this section and elsewhere in the specification, the clamping structure 2000 may be configured to collapse by collapsing one or more cells 2004. In some embodiments, the cells are all of the same approximate shape and size; however, in other embodiments, the cells are of different shapes and sizes.

The elongate strips 2006 may be made from one single material, such as those described elsewhere in the specification, or the elongate strips may be made from multiple materials. For example, elongate strips 2006 may comprise sections of more rigid material and sections of more flexible material. The elongate strips 2006 may be curved along their length so as to facilitate the curve of concave side and/or the convex side the clamping structure 2000. The elongate strips may be curved in same direction with the either of the concave side or the convex side. In some embodiments, each of the elongate strips may be curved in same direction so that they are arranged in parallel or semi-parallel fashion. The arch of the curves of the elongate strips 2006 may vary considerably, with some strips 2006 being highly curved while other are minimally curved or even straight. In some embodiments, the clamping structure may have one elongate strip between the concave side and the convex side. In other embodiments, the clamping structure may have zero, two, three, four or more elongate strips between the concave side and the convex side.

Similarly, the clamping structure 2000 can further comprise a plurality of intervening members 2010 connected to the elongate strips 2006. The intervening members 2010 may all be of a similar shape and size or they may be of a variety of shapes and sizes. The intervening members may be constructed from any material disclosed herein this section or elsewhere in the specification. Further, the intervening members may be constructed from multiple materials.

The clamping structure 2000 and all clamping structures described in this section or elsewhere in this specification can collapse on a variety of timescales in a dynamic fashion. In certain embodiments, the majority of the collapse may occur within the first few minutes upon application of negative pressure. However, after the initial collapse, the clamping structure may continue to collapse at a much slower rate, thereby applying increasing longitudinal tension over a long period of time and drawing the first end and the second together.

In certain embodiments, up to 90% of the collapse of the clamping structure may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the clamping structure can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure.

FIG. 2B is an illustration of a top view of the clamping structure embodiment of FIG. 2A. In some embodiments, the pattern of the clamping structure 2000 is designed in such a way as to facilitate maximum collapse of the clamping structure. In embodiments, maximum closure is in a direction perpendicular to the length of the elongate members and within the horizontal plane. As will be described in greater detail below, greater closure may be achieved by varying the length of the elongate strips 2006, the length of the intervening members 2010, and the shape of the cells 2004. The shape of the cells 2004 may comprise any shape described herein this section or elsewhere in the specification. For example, as depicted in FIG. 2A, the cells 2004 may be diamond-shaped or parallelepiped with smaller diamond-like shapes 2020 located within larger diamonds 2022. Such a construction may provide greater overall clamping of the clamping device 2000 to provide for maximum clamping. Additionally, the smaller diamond-like shapes 2020 located within larger diamonds 2022 can spread the load over a greater area.

FIG. 2C is a photograph of an embodiment of apparatus for use with negative pressure with the clamping structure 2000. In this embodiment, the clamping structure 2000 is contained within an air-tight plastic bag. However, in other embodiments, the apparatus may contain other means of forming air-tight seal to maintain the negative pressure environment around the clamping structure. For example, in some embodiments, a drape described in this section or elsewhere in the specification may be used with the clamping structure to maintain the negative pressure.

Any of the clamping structures described herein this section or elsewhere in the specification may be constructed from any suitable means. For example, the clamping structures may be constructed via molding or may be printed directly using 3D printing technology. In certain embodiments, the clamping structures of FIGS. 2A-C may be constructed from a single polymer via 3D printing. In some embodiments, the clamping structures may be constructed from a single polymer, two different polymers, three different polymers, or more than three different polymers. The clamping structures may be constructed from any material disclosed herein this section or elsewhere in the specification. The clamping structure can be made by cutting the structure out of a solid block of material. Methods used for cutting can include, for example, water jet cutting, laser cutting, or die cutting. The clamping structures may be cut to size along the walls of the cells 2004. For example, the intervening members along the outside face of elongate strips 2006 can be cut off to appropriately size the clamping structure. The clamping structure may be cut along the walls, along any portions of the elongate strips, and/or along any portions of the intervening members. In certain embodiments, the clamping structure may be created from a mold.

In some embodiments, the clamping structure 2000 of FIGS. 2A-C can be configured to include perforations or detachable sections that allow portions of the device to separate from the remainder of the device. For example, perforations may be incorporated into the joints 2900 between various cells 2004 contained within the clamping structure 2000, allowing for the removal of individual rows or cells to alter the shape of the clamping structure 2000.

In some embodiments, the clamping structure 2000 of FIGS. 2A-C may have holes or notches on the elongate strips 2006 and/or intervening members 2010 defining cells 2004, such that cells are in fluidic communication with each other. This feature may act as a fluid pathway and help propagation of negative pressure along the clamping structure, thus facilitate collapsing of the clamping structure 2000.

Applicable to all clamping structures described in this section or elsewhere in the specification, the clamping structure may be tearable such that the clamping structure may be shaped into any desirable shape. In some embodiments, the clamping structure may be torn at the intersections between intervening members and elongate strips, while in further embodiments, the elongate strips or intervening members may be torn at any suitable position.

FIGS. 3A-4C: Design and Operation of Clamping Structure

Figure 3A:
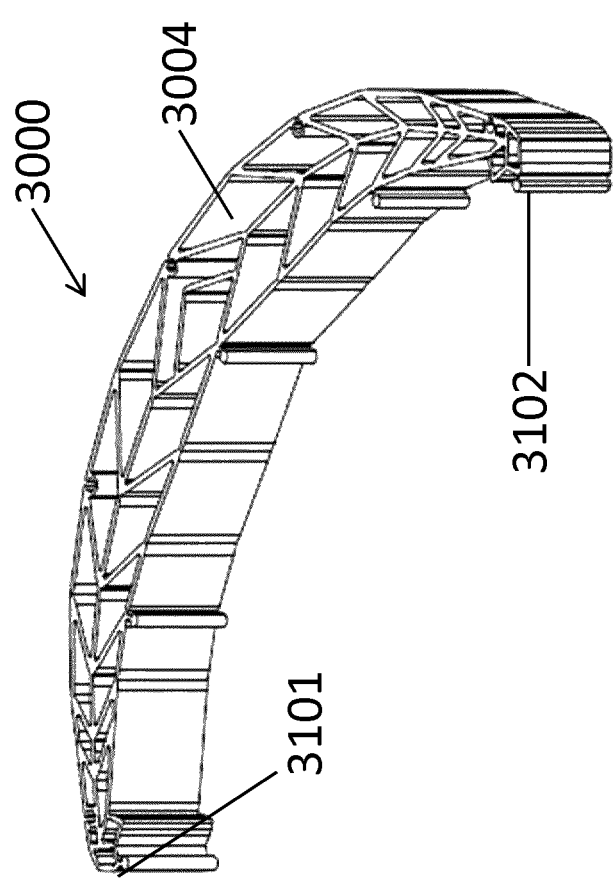
FIGS. 3A-C illustrate perspective views of an embodiment of a clamping structure in a natural state, a half-collapsed state, and a collapsed state.
Figure 3B:
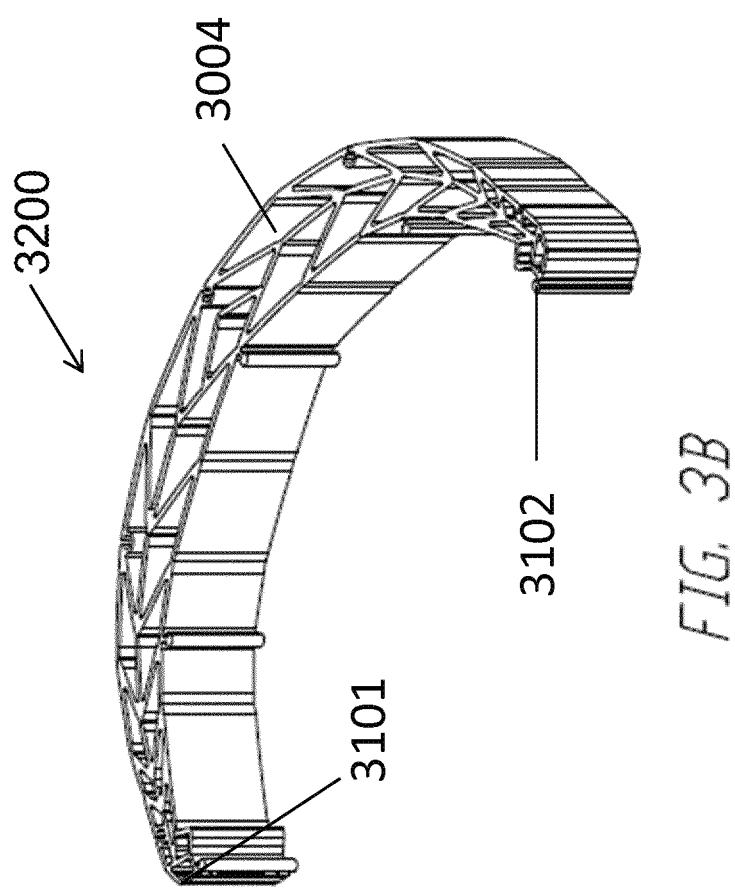
Figure 3C:
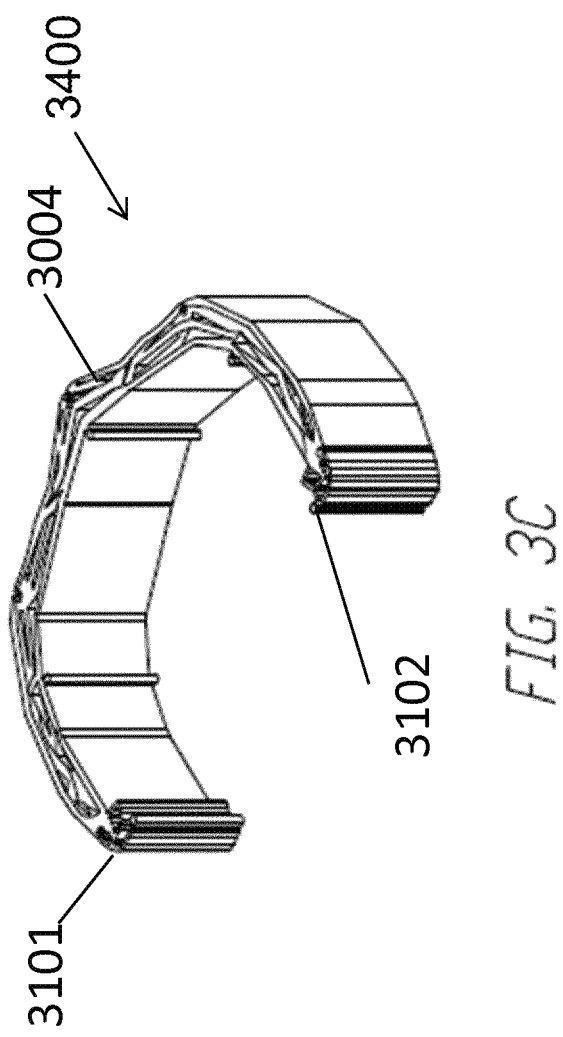

FIGS. 3A-4C illustrate an embodiment of a clamping structure 3000 having a cell configuration as described above. FIGS. 3A-C illustrate perspective views of the transformation of an embodiment of the clamping structure 3000 before application of negative pressure, the clamping structure 3200 during collapse with or without negative pressure, and the clamping structure 3400 after collapse with or without negative pressure. In some embodiments, as shown by FIGS. 3A-C, when cells 3004 collapse with or without negative pressure, the curvature of the elongate strips of the clamping structure increases and the distance between first end 3101 and the second end 3102 decreases. In some embodiments, the first end and the second end completely touches each other upon the collapse of the clamping structure. In other embodiments, the distance between the first end and the second end after collapse is less than 80%, 70%, 60%, 50%, 40%, 30%, 20%, or 10% of the original distance between the first end and the second end. In some embodiments where one or more object is placed between the first end and the second end, the clamping structure may grab the one or more object. In other embodiments where objects are attached to the first end and the second end, the clamping structure may pull objects attached to the first end and the second end closer.

Figure 3D:
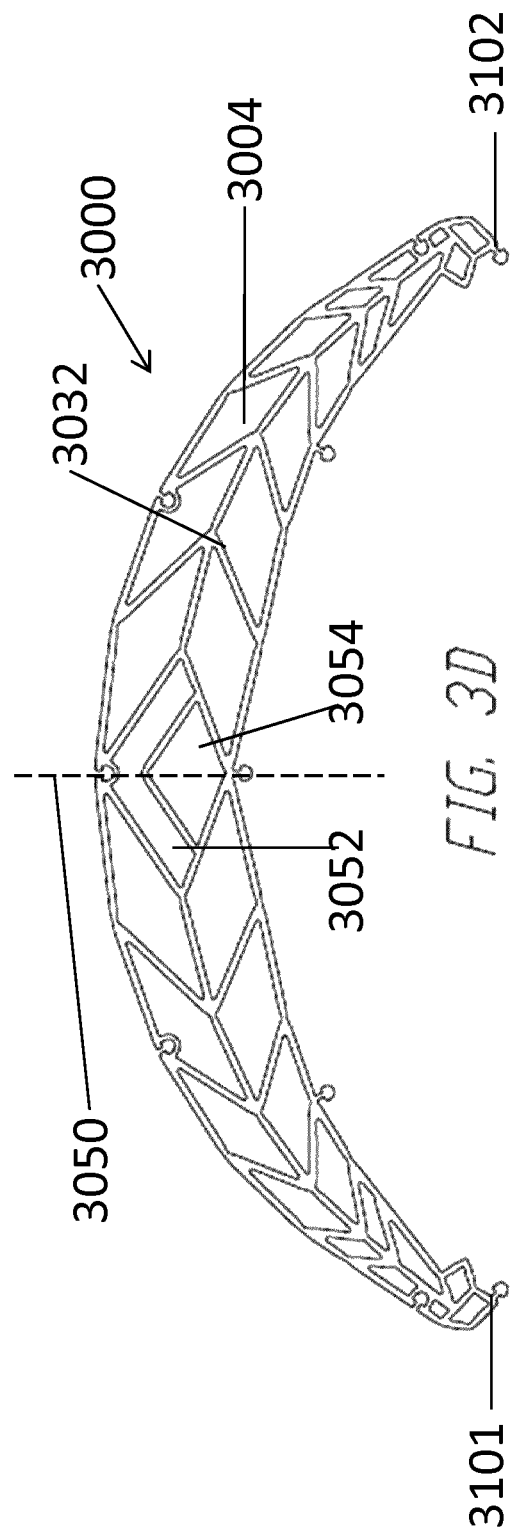
FIGS. 3D-F illustrate top views of an embodiment of a clamping structure in a natural state, a half-collapsed state, and a collapsed state.
Figure 3E:
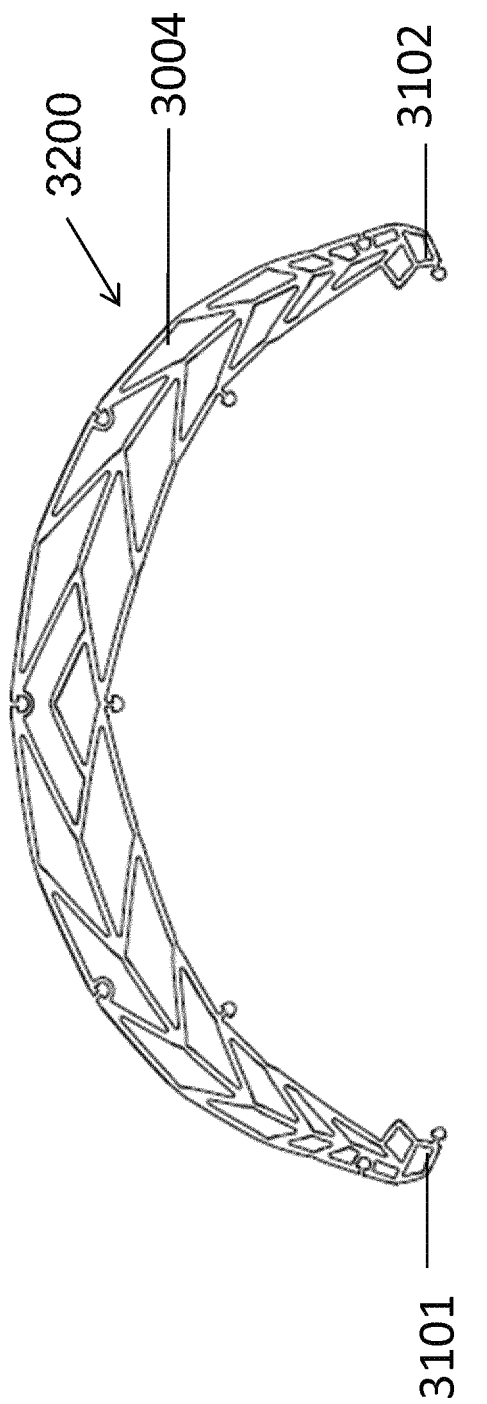
Figure 3F:
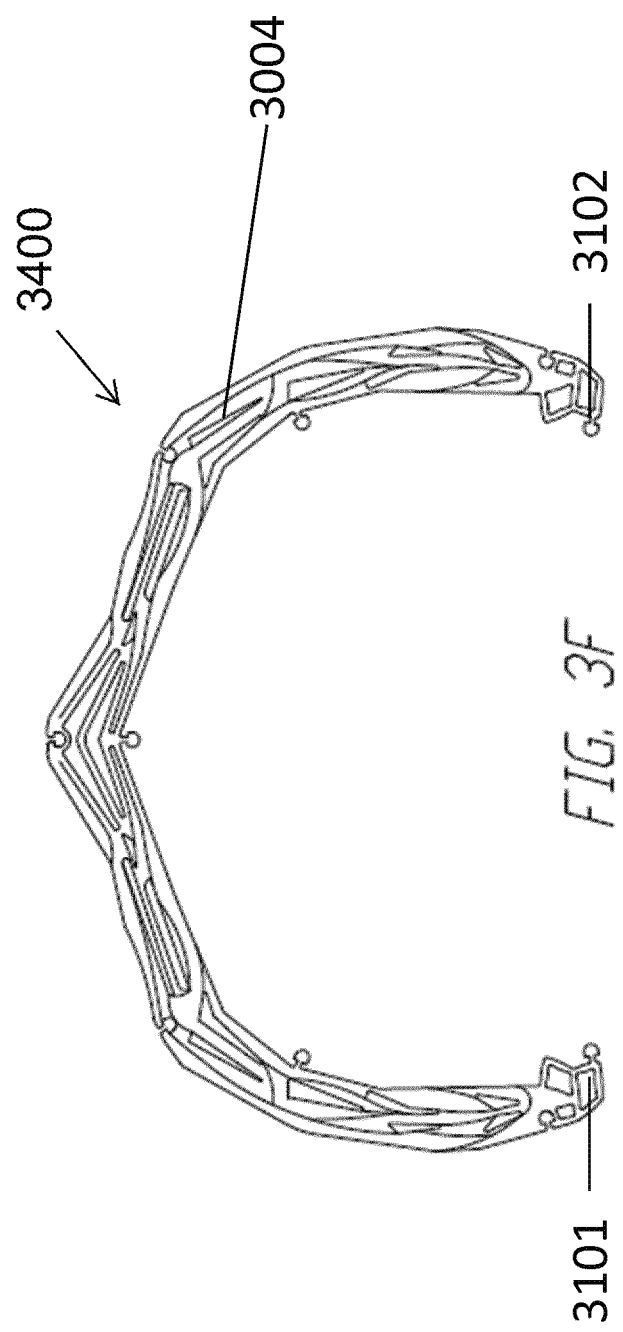
Figure 3G:
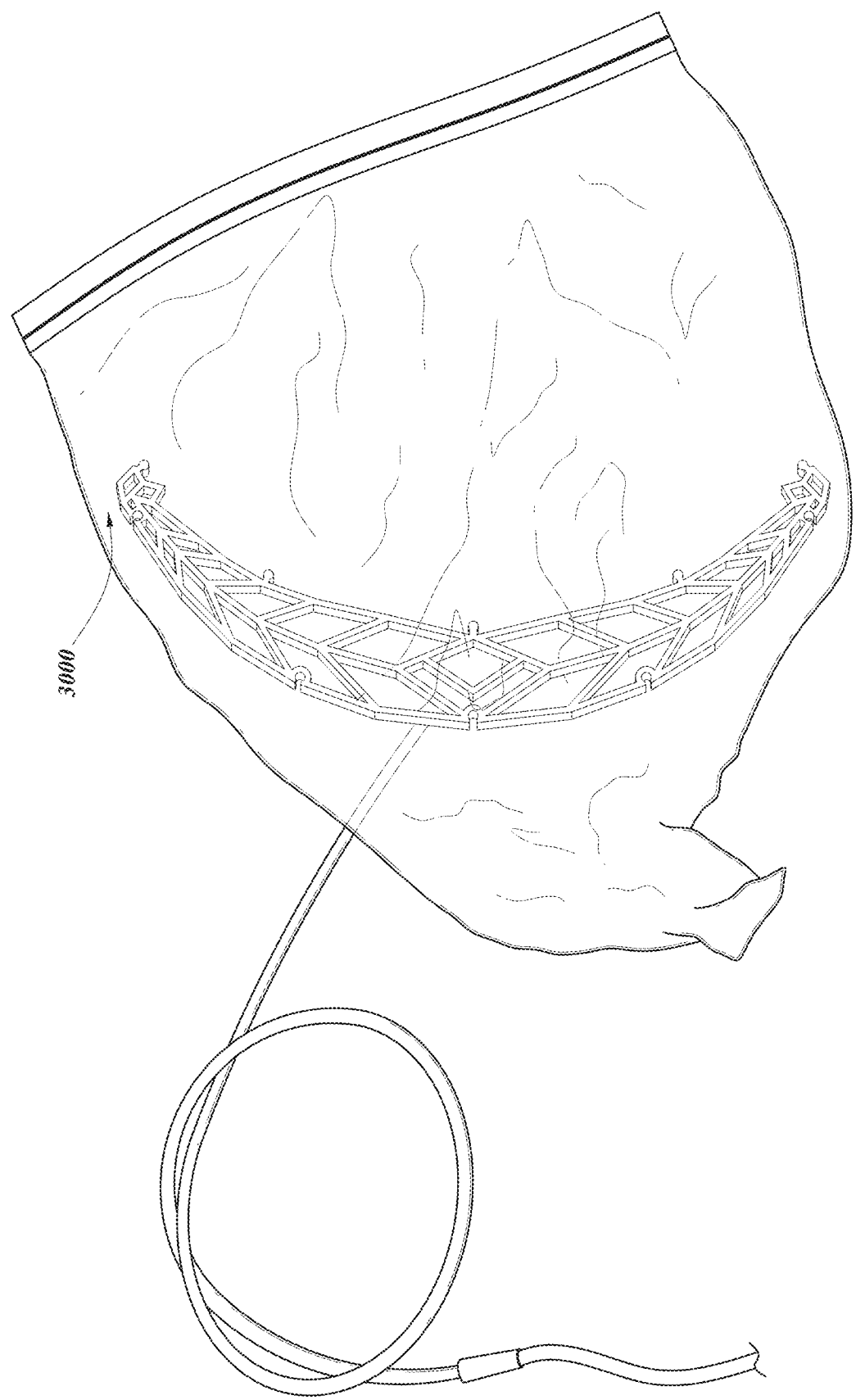
FIGS. 3G-H depict an embodiment of an apparatus for use with negative pressure having a clamping structure in a natural state and a collapsed state.
Figure 3H:
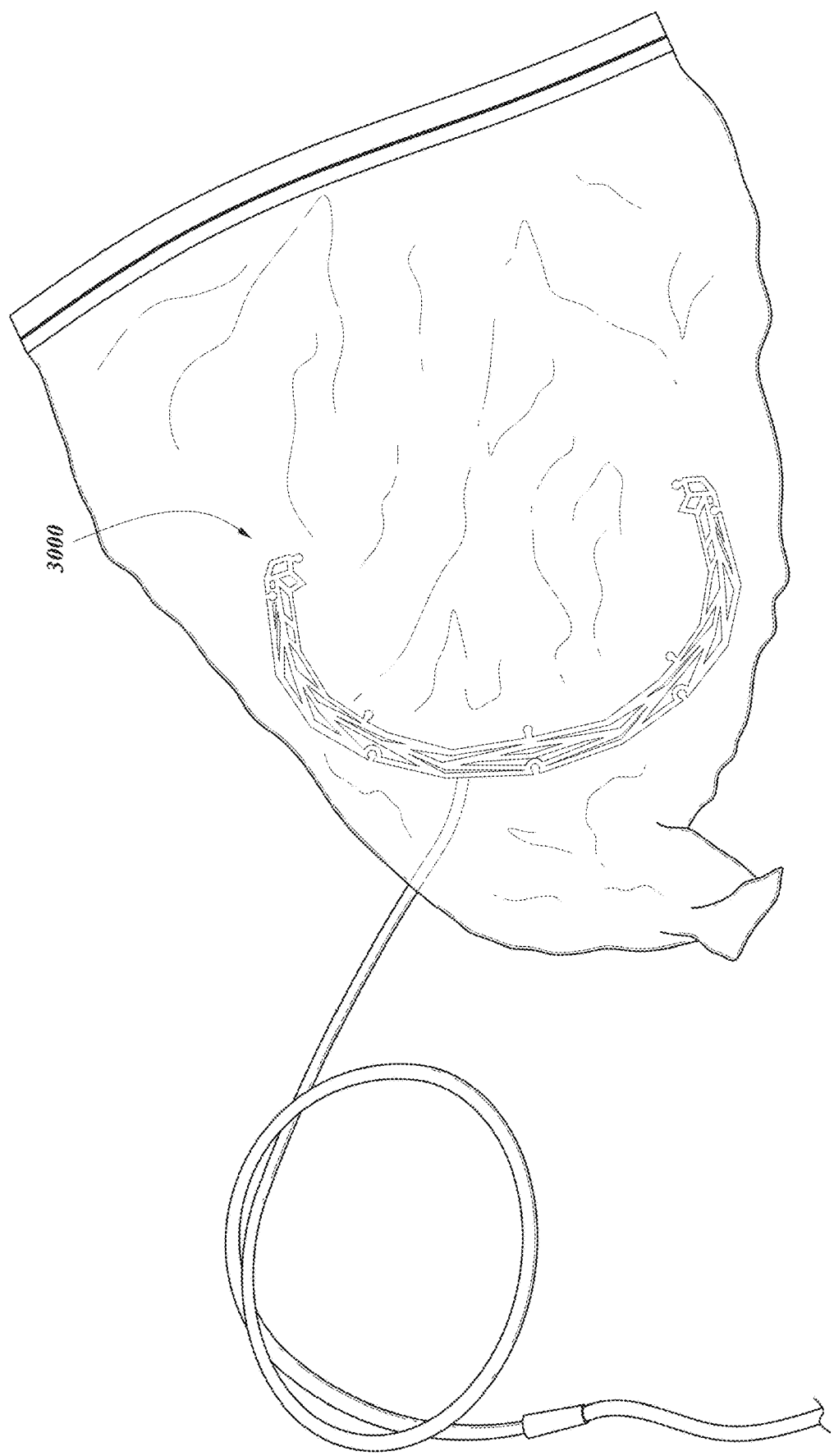

To facilitate various types and degree of transformation (for example, maximum clamping) the shape, size, and location of the elongate strips, intervening members, and cells may be determined via various methods. FIGS. 3D-F illustrate a top view of the embodiment of FIGS. 3A-C. For example, as depicted in FIG. 3D, each collapsible cell 3004 may have four sides, and each intersection between an intervening member(s) and/or elongated strip(s) may be modeled via pin-joints 3032. As depicted in FIGS. 3A-F, the clamping structure 3000 may be modeled to collapse from an open state to a semi-collapsed state 3200, and to a fully collapsed state 3400. In some scenarios, maximum collapse down to the embodiment depicted by FIGS. 3C, 3F and 3H may be desirable to maximize clamping by drawing the first end and the second end of the clamping structure close together as possible. FIGS. 3G-H are photographs of an embodiment of the clamping structure 3000 before negative pressure is applied, and the clamping structure 3400 after negative pressure is applied.

As illustrated in FIG. 3D, in certain embodiments, the process of determining the optimal shape, size, and location of the elongate strips, intervening members, and cells for clamping may be facilitated by modeling the clamping structure as a mirrored pattern on opposite sides of a mirror line 3050 (which may also be referred to as the transverse axis, perpendicular to a length of the clamping structure), thereby making the curve and collapse of the clamping structure symmetrical. The mirror line may be located in any suitable location within the clamping structure, such as diagonally across the clamping structure. In certain embodiments, this method may lead to large diamond-shaped cells near the center line. These large diamond-shaped structures 3052 may be further subdivided to further support the clamping structure by including smaller diamond shapes 3054 within larger shapes. In some embodiments, these smaller shapes 3054 within a larger shape 3052 may comprise any shape disclosed herein this section or elsewhere in the specification. The larger cells may be further subdivided by two smaller shapes, three smaller shapes, four smaller shapes, or more than four smaller shapes. In some embodiments, the clamping structure may contain multiple mirror lines, thereby having multiple subsections that are symmetrical or different.

Figure 4A:
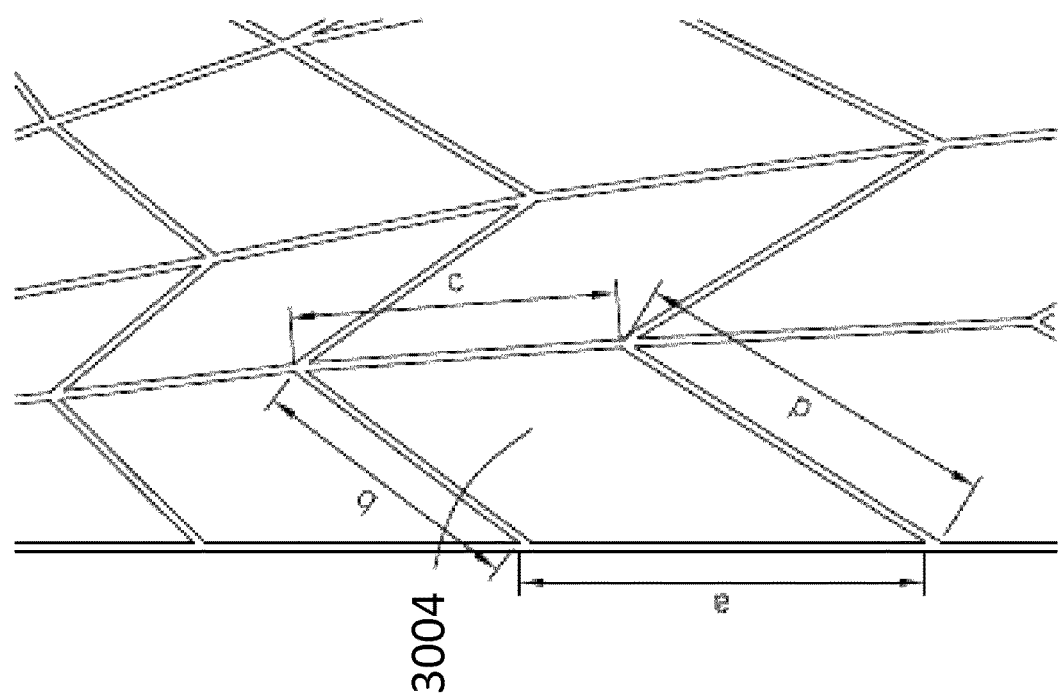
FIGS. 4A-C illustrate an embodiment of a method for determining the size and shape of cells within a clamping structure.

As illustrated in FIG. 4A, for a four-sided cell to completely collapse, it must follow a simple formula: $a+b=c+d$, where a, b, c, and d are the lengths of individual sides of a single cell within the clamping structure such as the cell 3004 of FIG. 3G. When members c and b collapse together, then d and a collapse together. Such a formula may be the basis for developing a pattern for a clamping structure that maximizes collapsibility.

Figure 4B:
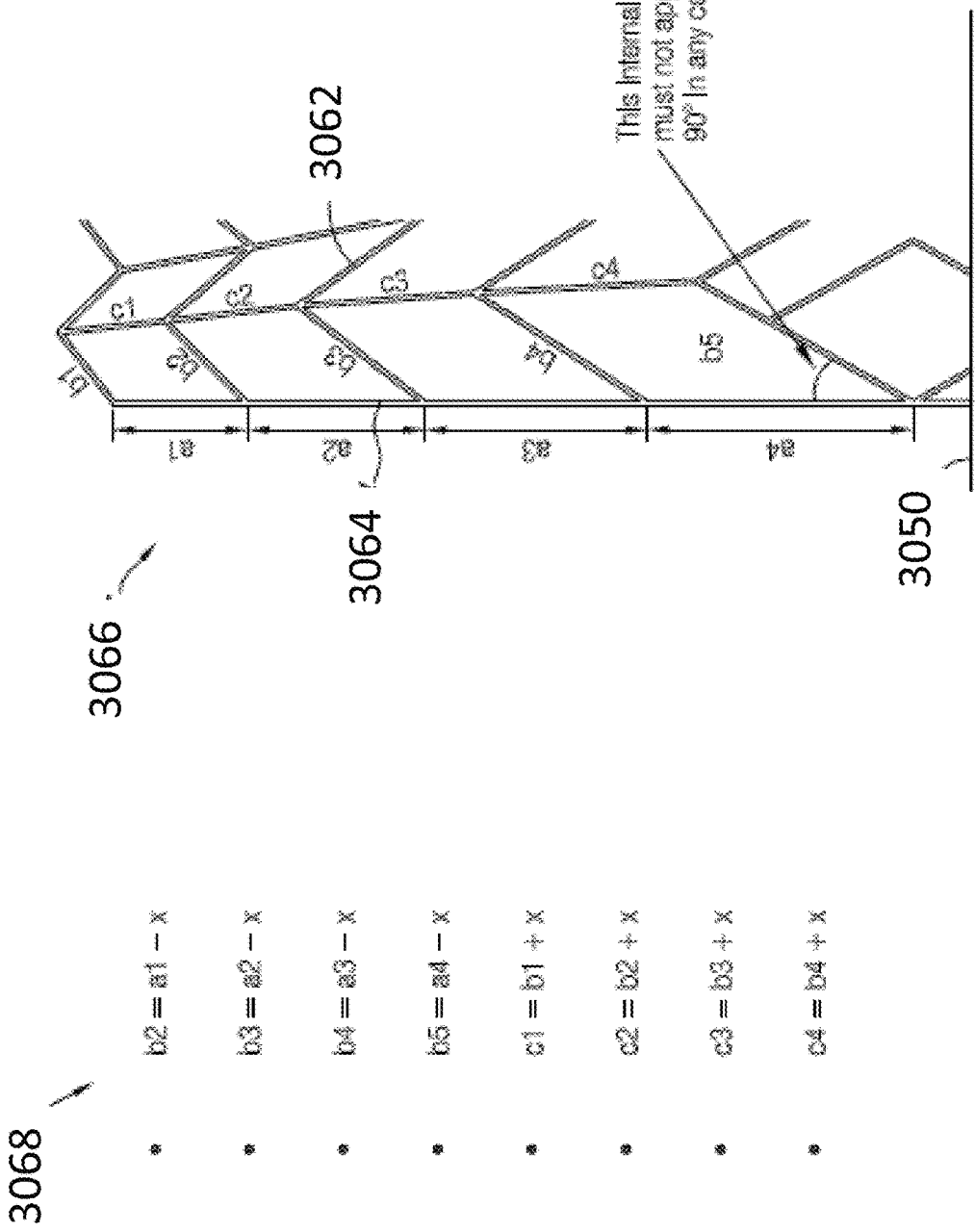
Figure 4C:
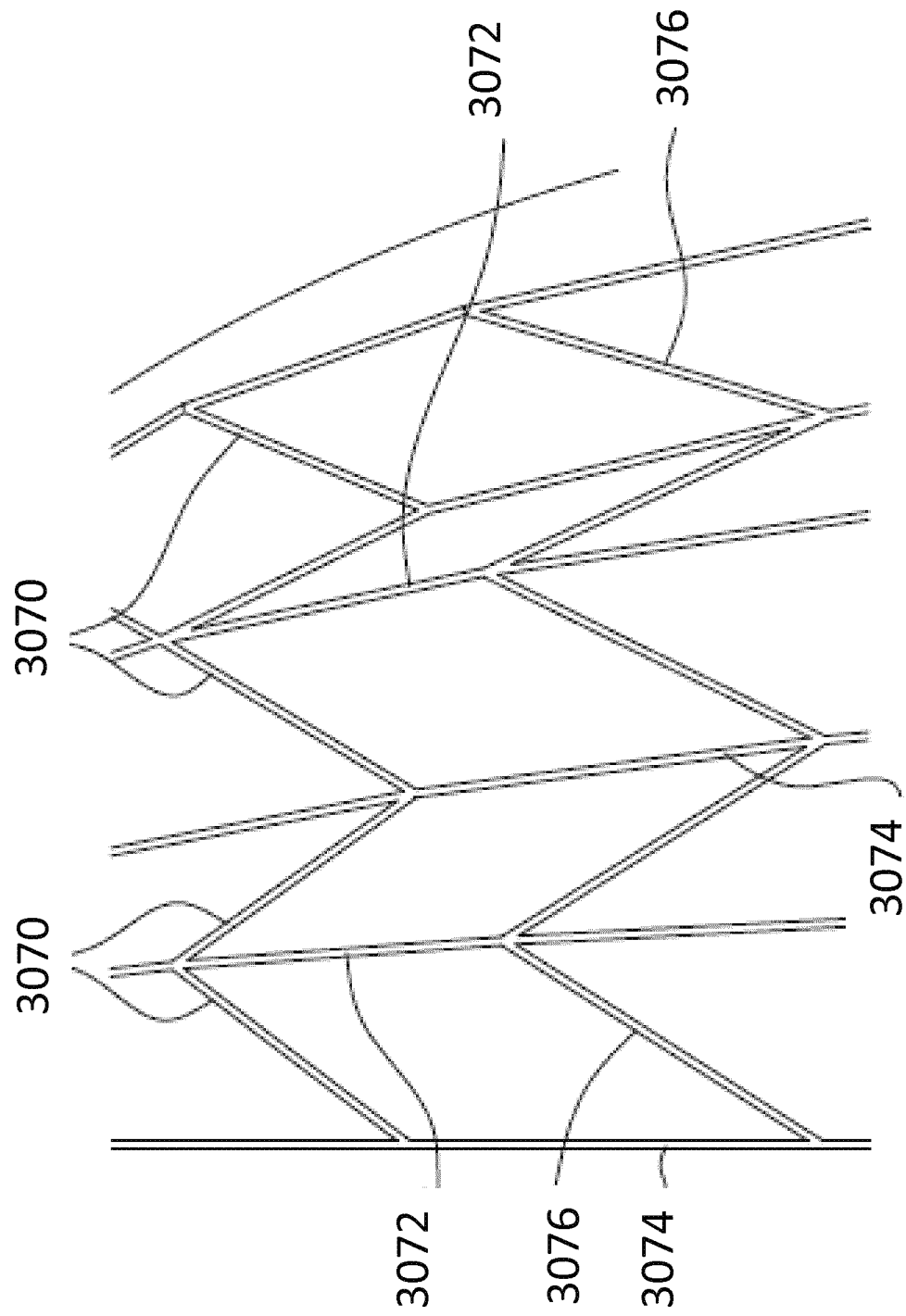

Further, as illustrated in FIG. 4B, elongate strip cell sections were progressively lengthened ($a4>a3>a2>a1$) towards the horizontal mirror line 3050, thereby achieving a curve following the curve of elongated strips in the clamping structure while preventing any of the intervening members 3062 from becoming perpendicular to the elongate strips 3064 (i.e. having an internal angle of 90 degrees). As illustrated in FIG. 4B, a value for b1 may be chosen, at which point an arbitrary offset value x may also be chosen to ease the construction of the various cell geometries. Using the progressive values for a1 through a4, illustrated visually in FIG. 3H 3066, values for b1-b4 may be calculated 3068. Using calculated values derived from equations 3068 for the various walls of the individual cells allows for the design of a clamping structure that collapses completely, such as those depicted in FIGS. 3A-F.

In some embodiments, a method for generating a clamping structure design may include steps to speed up the initial geometry construction. For example, if all members from left to right are in a specific row, as visualized by intervening members 3076 in FIG. 4C, a pattern then emerges where alternating vertical members are also the same length. Walls of the same length are indicated by their respective labels 3070, 3072, 3074, and 3076. Once the initial design is generated then individual cells may be modified by lengthening, shortening, removing or inserted according to the formulas of FIG. 4B to achieve the desired shape of the overall clamping structure.

FIGS. 5A-7B: Detachable Segments

Figure 5A:
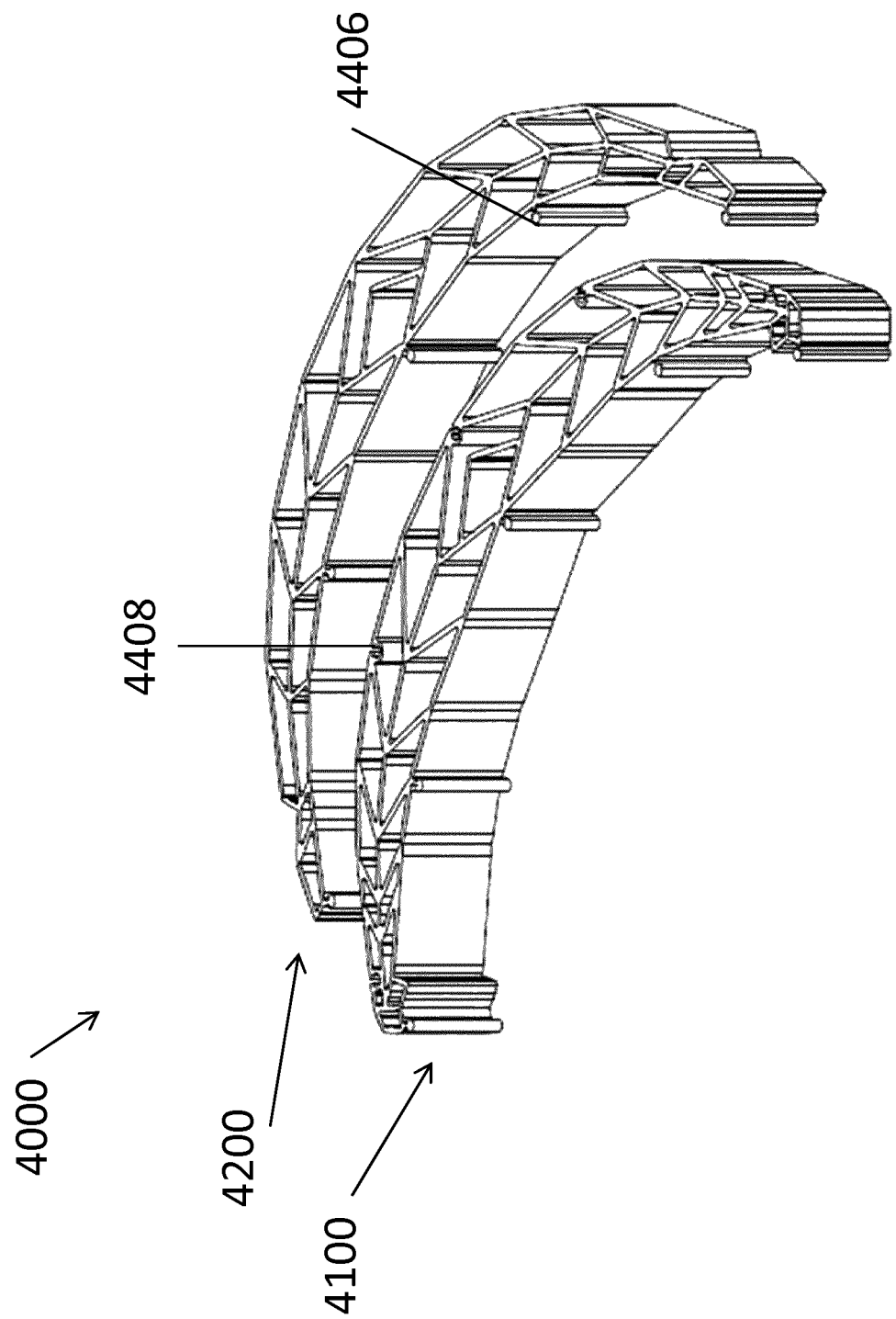
Figure 5B:
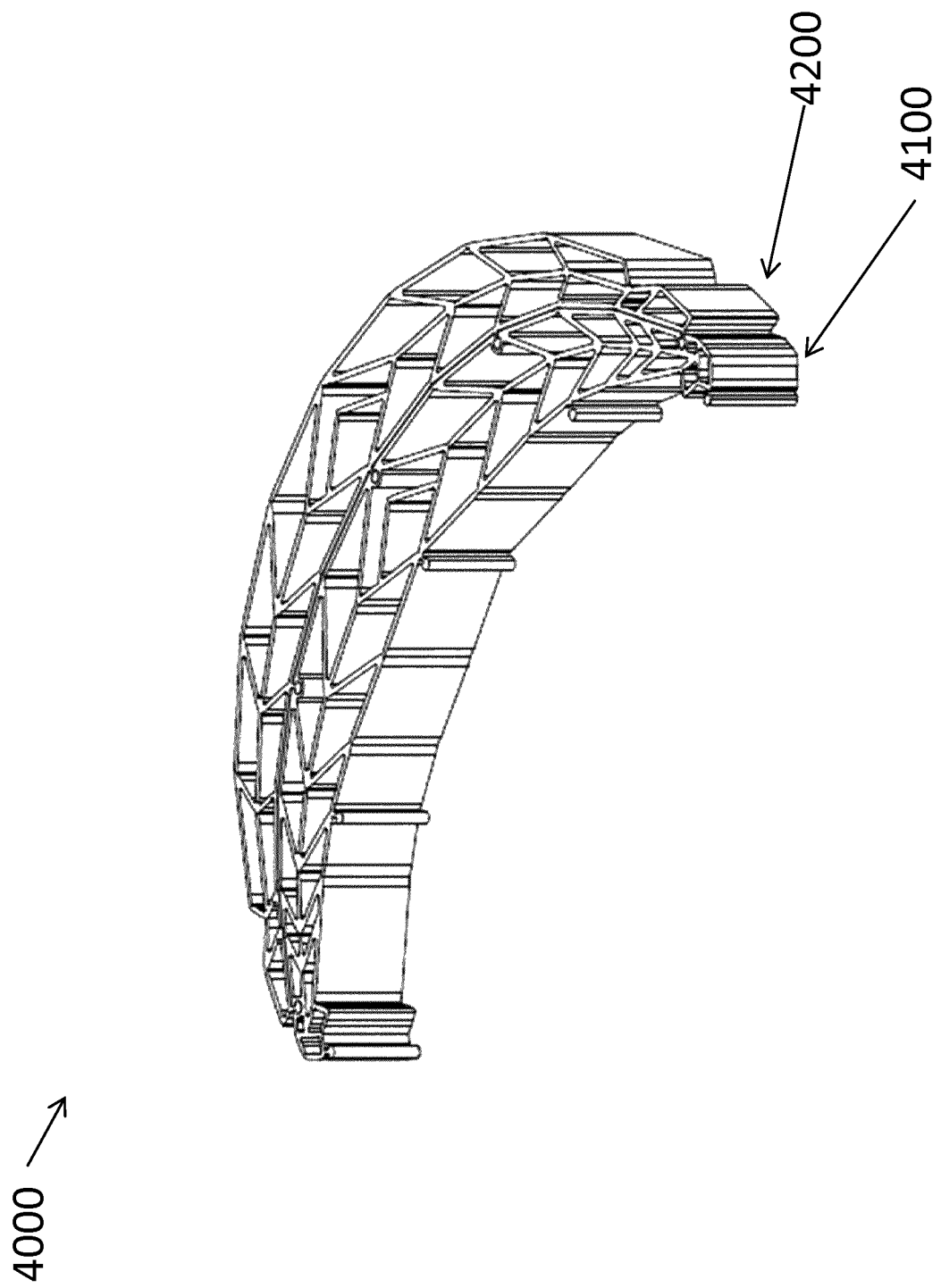

FIGS. 5A-B illustrate an embodiment of a clamping structure 4000, similar to the clamping structures disclosed previously in FIGS. 2A-2C, 3A-B, and 4A-C. Here, clamping structure 4000 comprises inner segment 4100 and a detachable segment 4200. In some embodiments, the detachable segment 4200 at least partially surrounds the inner segment 4100. In some embodiments, each of the segments may have a crescent shape. To adjust the clamping structure to desired shape or size, in embodiments, the detachable segment of the clamping structure 4200 may be removed from the overall structure to form a smaller clamping structure such as the inner segment 4100. In certain embodiments, there may be at least: one, two, three, four, five, six, seven, eight, nine or ten removable segments.

One of skill in the art will understand that the detachable sections of the clamping structures of FIGS. 5A-7B, and any clamping structure disclosed herein this section or elsewhere in the specification, may be removed in any suitable direction. For example, the clamping structure may be configured such that the detachable section(s) may be removed horizontally within an x-y plane parallel to the longest dimension of the clamping structure. In certain embodiments, the clamping structure may be configured such that detachable sections may be removed in a vertical direction in the z axis, perpendicular to the x-y plane. The clamping structure may have at least one detachable section removable in a horizontal direction and one section removable in a vertical direction. The detachable section(s) may be attached to the clamping structure in such a manner that the detachable section(s) may only be removed in a single direction, such as by the use of slots and/or channels as the attachment and receiving elements.

In embodiments, the clamping structure segments may be cut from the clamping structure 4000 to produce a smaller structure. In certain embodiments, the clamping structure may have pre-cuts along the shape of the segments 4100 and 4200 to allow the segments to be tearable and easily removed by hand from the clamping structure. The detachable segments may be adhered to the remainder of the clamping structure via adhesive, Velcro®, or other suitable adhesive means. In certain embodiments, the removable sections may be held together by the tightness of the structures squeezing together and/or via friction. In some embodiments, magnets and/or suction cups may be used to keep the segments together.

Figure 5D:
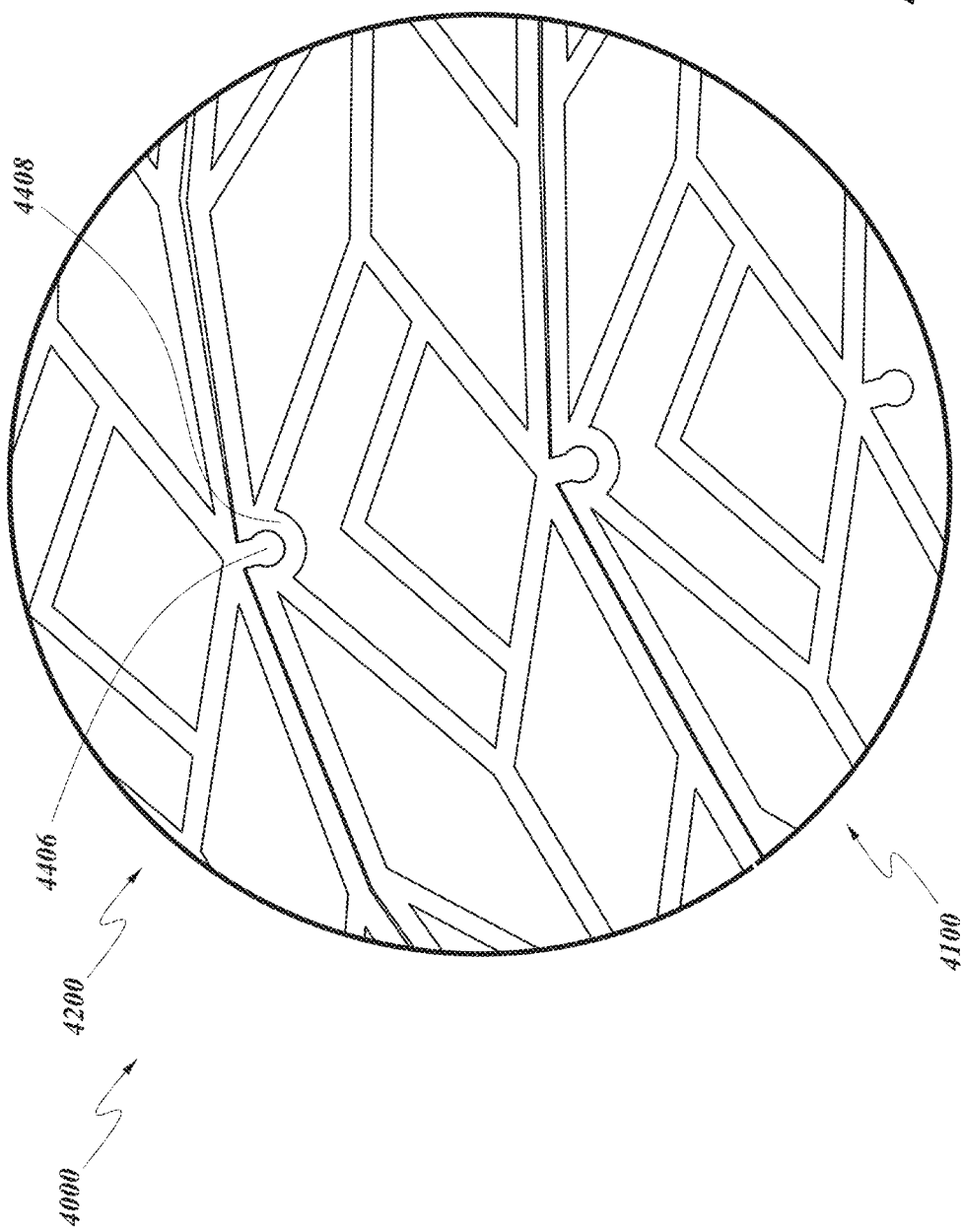

As shown in FIGS. 5A-D, in some embodiments, detachable segments 4200 may comprise one or more attachment elements 4406, which may be in the form of prongs, hooks, tongues, screws, nails, or other suitable attachment means. FIGS. 5C-D are photographs of such embodiments. As shown in FIG. 5C-D, the attachment elements 4406 attach to receiving elements 4408 of the inner segment 4100 which may be in the form of grooves, holes, windows, or any suitable means. For example, FIG. 5C-D depicts an embodiment of a clamping structure 4000 where the attachment elements 4406 are tongues which fit into the receiving elements, which are grooves 4408. The attachment elements serve to maintain attachment of the detachable segment to the inner segment or another detachable segment until the clamping element is re-sized by applying suitable force to separate the attachment elements from the receiving elements. In certain embodiments, detachable segments and inner segment may comprise both attachment elements and receiving elements. For example, a detachable segment may comprise attachment elements on one side and receiving elements on the opposite side to allow the detachable elements to be stacked one after another. In certain embodiments, segments may comprise at least about 1, 2, 3, 4, 5, 6, 7, 8, 10, 15, 20, 30, or more than 30 attachment elements. In some embodiments, segments may comprise at least about 1, 2, 3, 4, 5, 6, 7, 8, 10, 15, 20, 30, or more than 30 receiving elements.

Figure 5E:
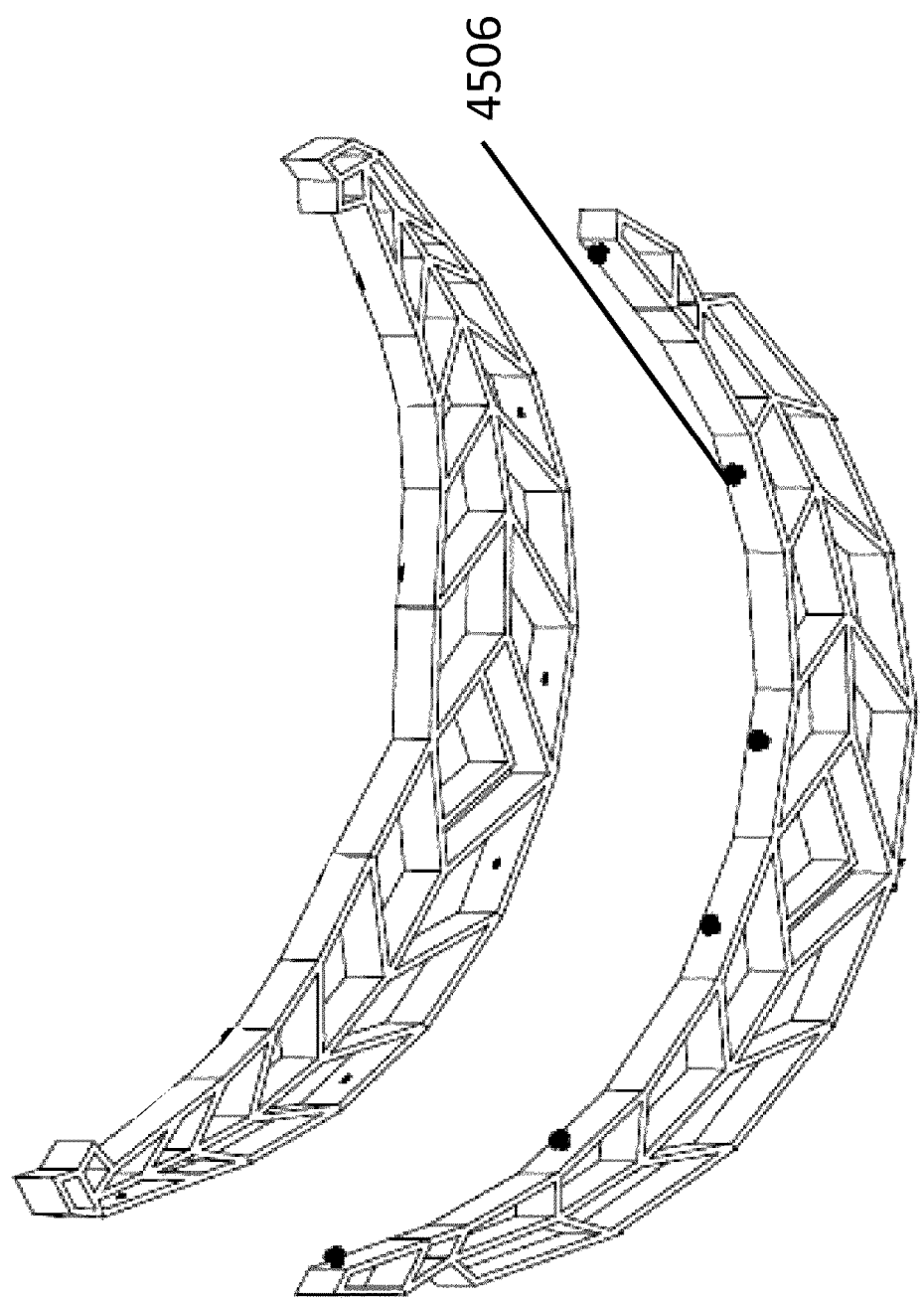
Figure 5F:
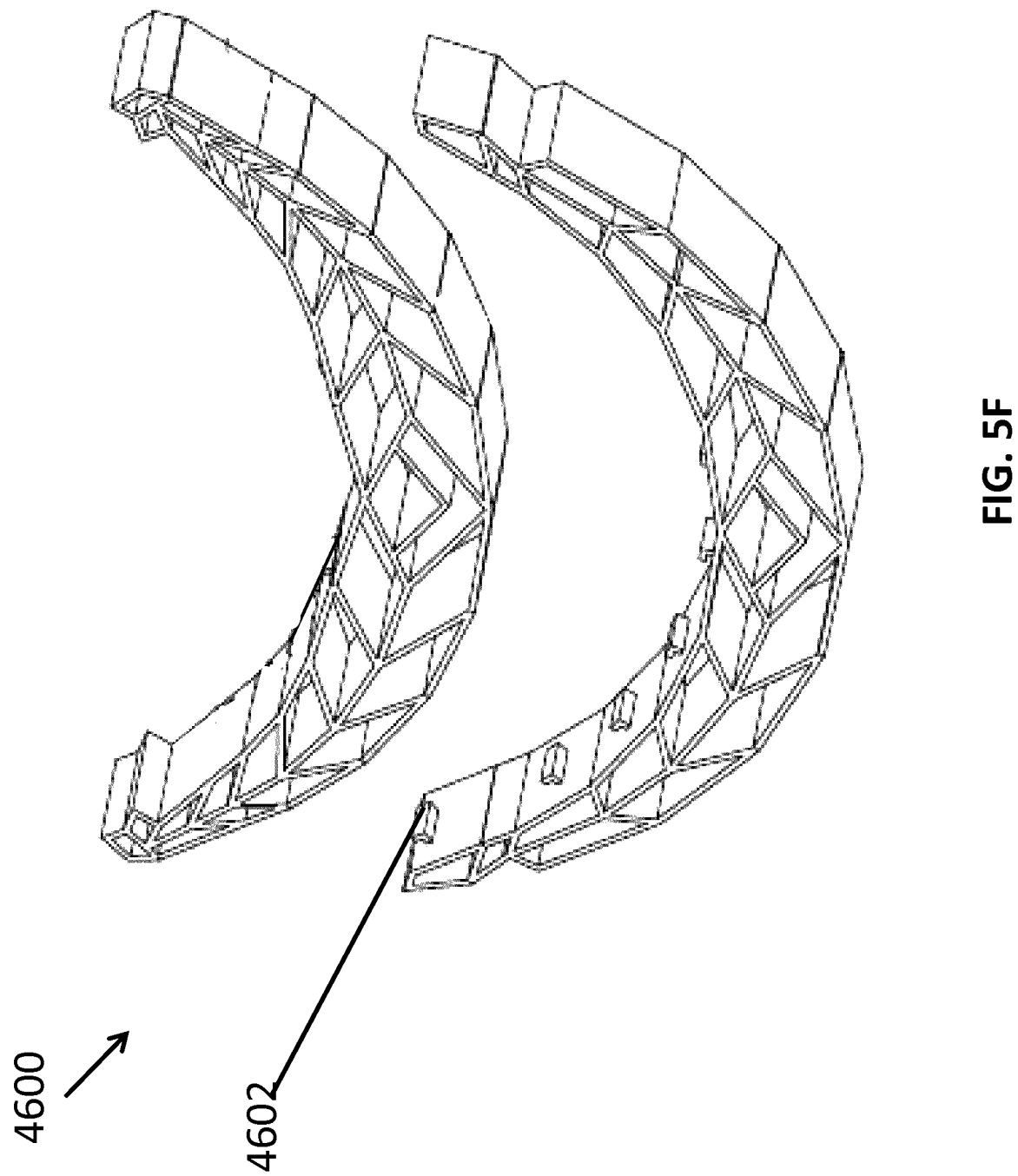
Figure 5G:
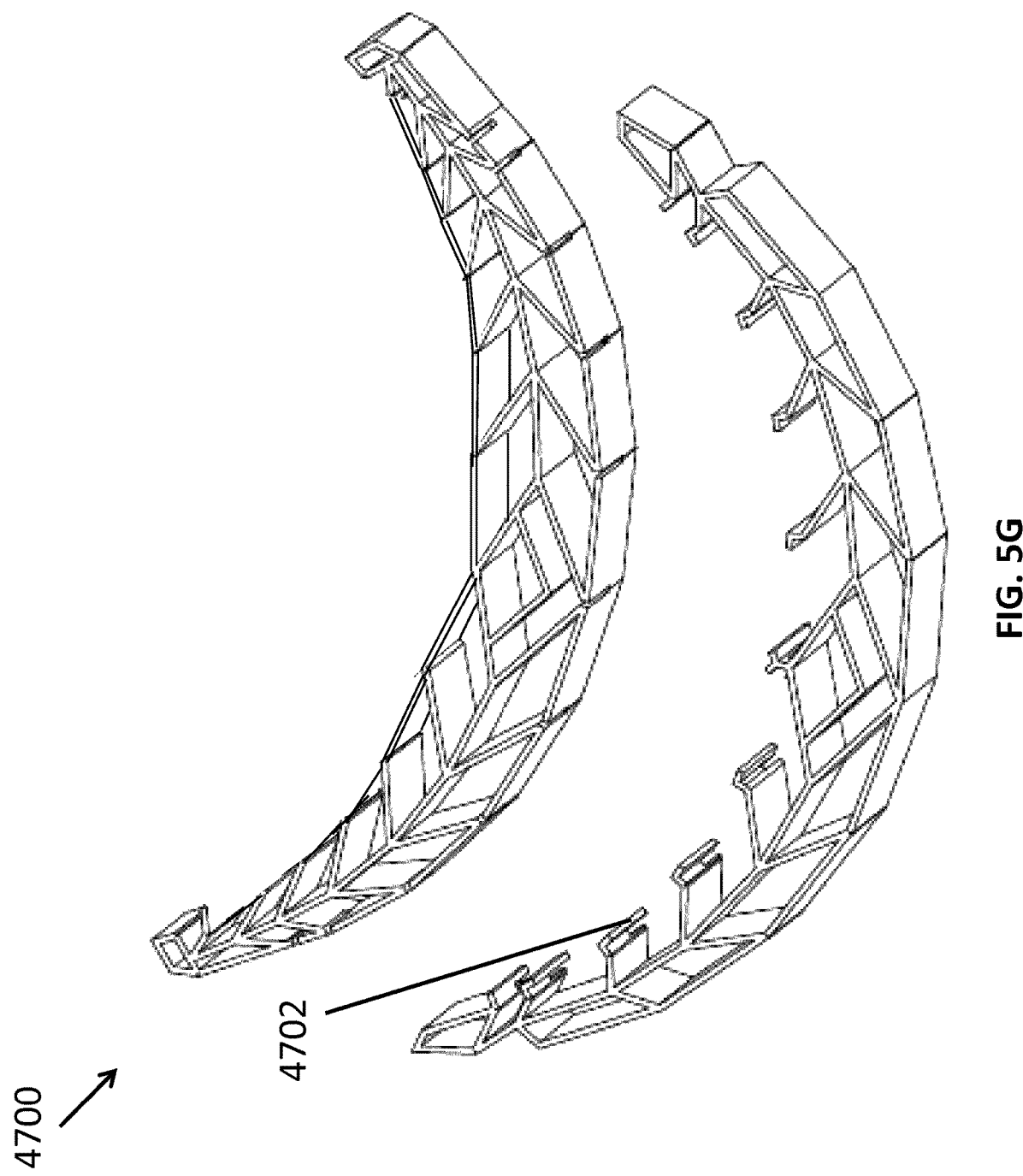
Figure 5H:
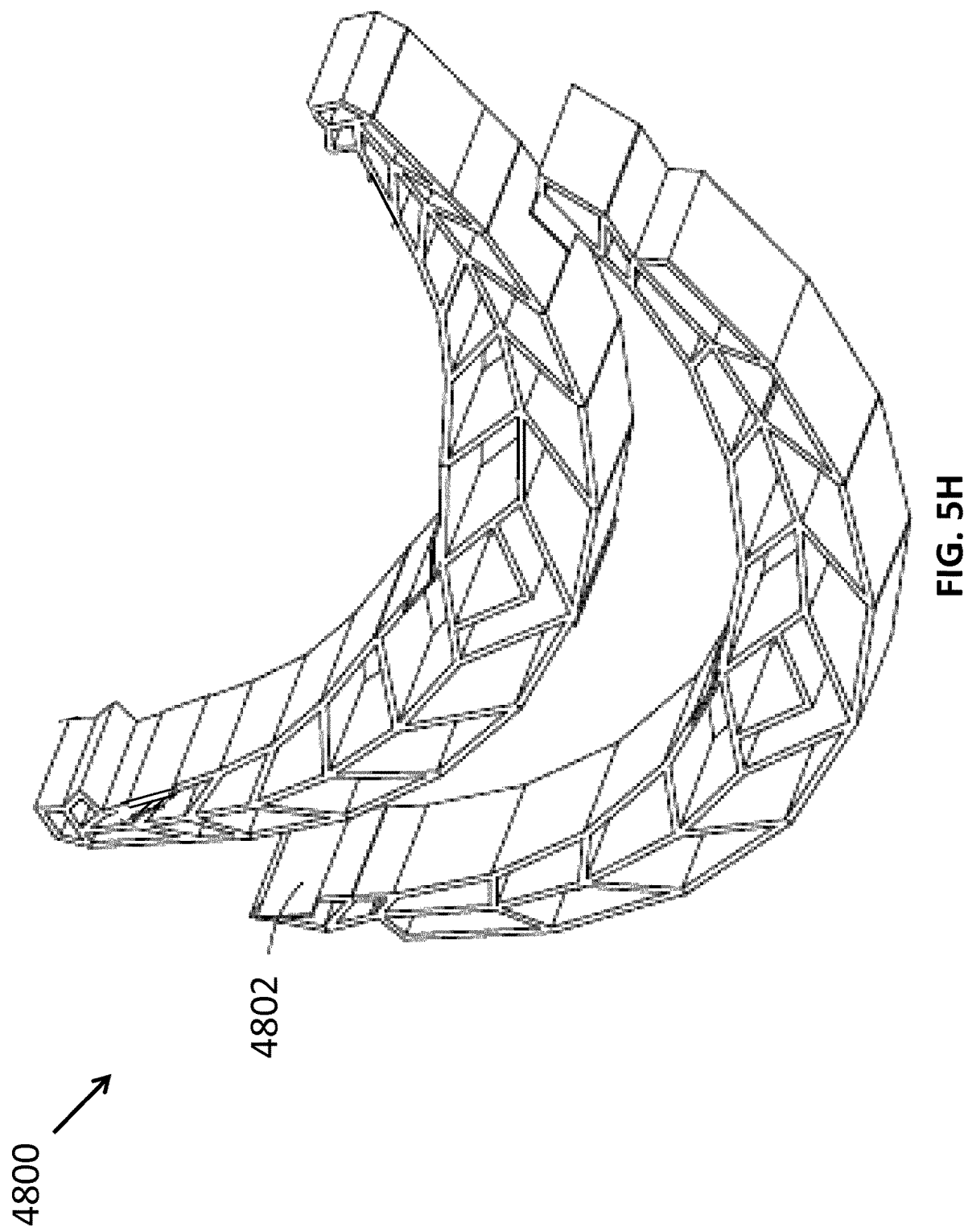

FIG. 5E depicts an embodiment of a clamping structure 4500 where the attachment elements 4506 are prongs. FIG. 5F depicts an embodiment of a clamping structure 4600 where the attachment elements 4602 are claws which fit into the receiving elements, which are grooves 4604. FIG. 5G depicts an embodiment of a clamping structure 4700 where the attachment elements 4702 are hooked and the receiving elements are configured to receive the hooks. FIG. 5H depicts an embodiment of a clamping structure 4800 where adhesive 4802 may be applied to certain areas of the detachable segments for adhesion to the outer surfaces of other detachable segments or the inner segment. Adhesive may also be applied to the inner segment.

Figure 5I:
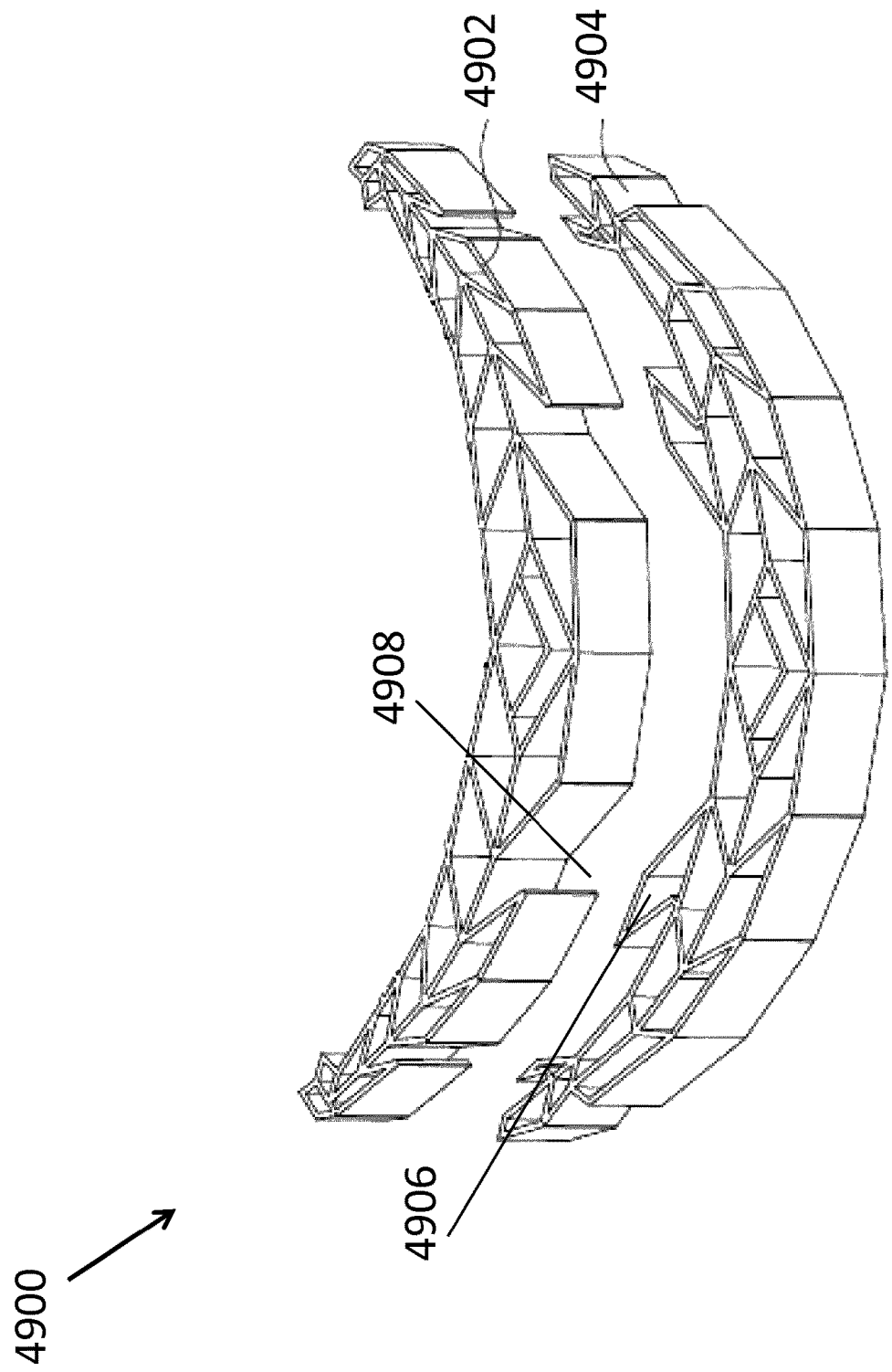

FIG. 5I depicts a clamping structure 4900 similar to the clamping structures of FIGS. 5A-5H. Here the detachable segments 4904 comprise extended cells 4906 which fit into recesses 4908 of inner segment 4902 or another detachable segment 4904. In embodiments, the extended cells are configured to snap fit into the recesses, such that the different segments can be separated from one another by the application of force. For example, separation can occur by the application of force by a user.

In certain embodiments, the detachable segments such as those disclosed above in relation to FIGS. 5A-I may be packaged within a separate kit from the clamping structure. The separately packaged detachable segments may comprise attachment elements and/or receiving elements such as those disclosed herein this section or elsewhere in the specification. Such separately packaged detachable segments may then be added to main clamping structure to increase the size and/or alter the shape of the clamping structure. In certain embodiments, the separate kit(s) of detachable segments may contain one detachable segment, two detachable segments, three detachable segments, four detachable segments, five detachable segments, or more than five detachable segments. In some embodiments, the detachable segments may be in the form of a crescent.

Clamping structures may collapse in different fashion depending on the shape of the clamping structure. For example, in some embodiments, when the curvature of a clamping structure increases upon collapse of cells, the increase of the curvature is greater when the difference between the length of the concave side and the convex side is greater. The difference between the length of the concave side and the convex side may be adjusted with the installation or removal of detachable segments. For example, in FIGS. 5A-B, the difference between the length of the concave side and the convex side is greater in the clamping structure 4000 than in the inner segment 4100.

Figure 6A:
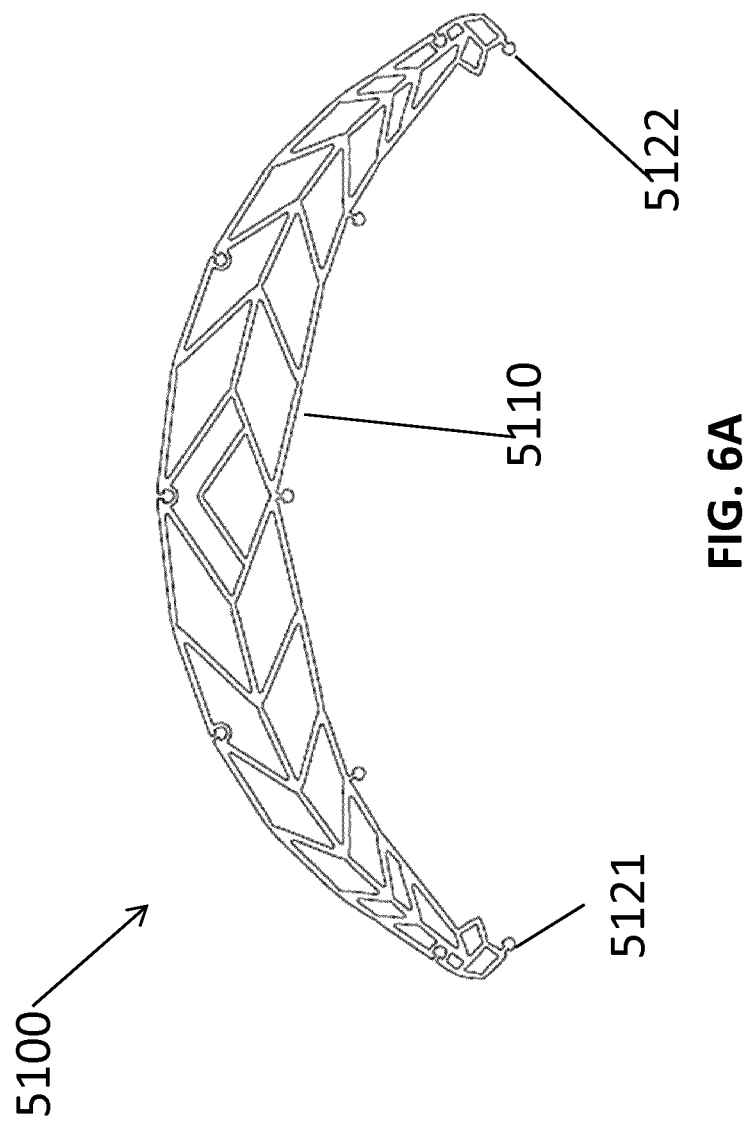
FIGS. 6A-B illustrate an embodiment of an inner segment of a clamping structure in a natural state and a collapsed state.
Figure 6B:
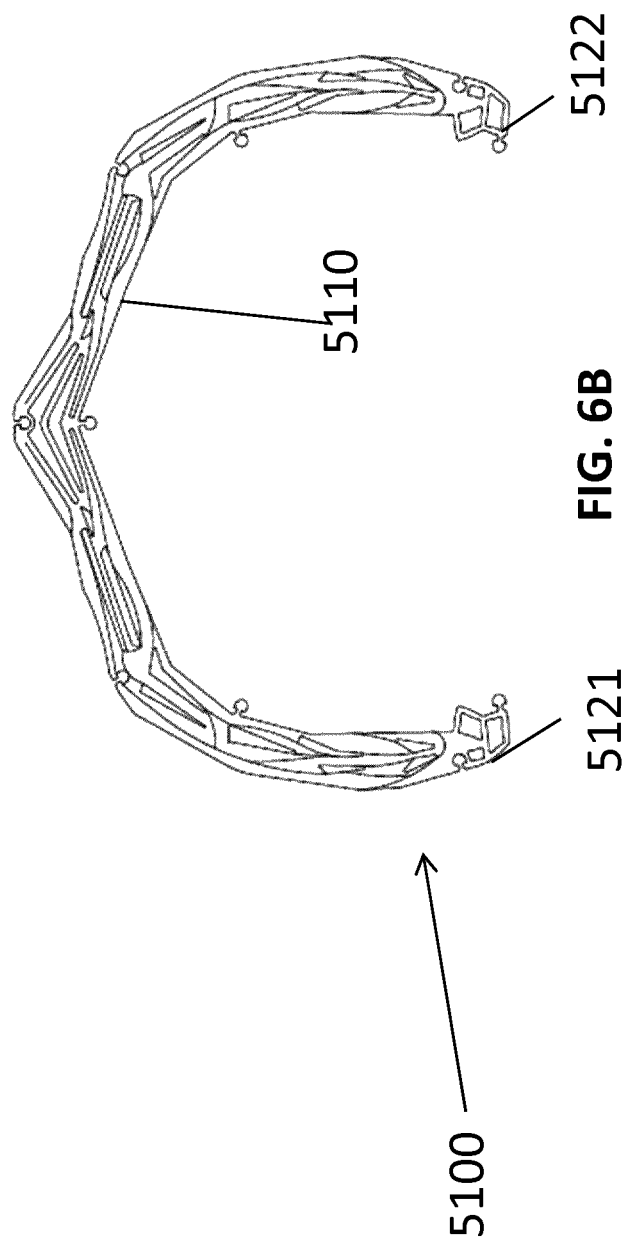
Figure 7A:
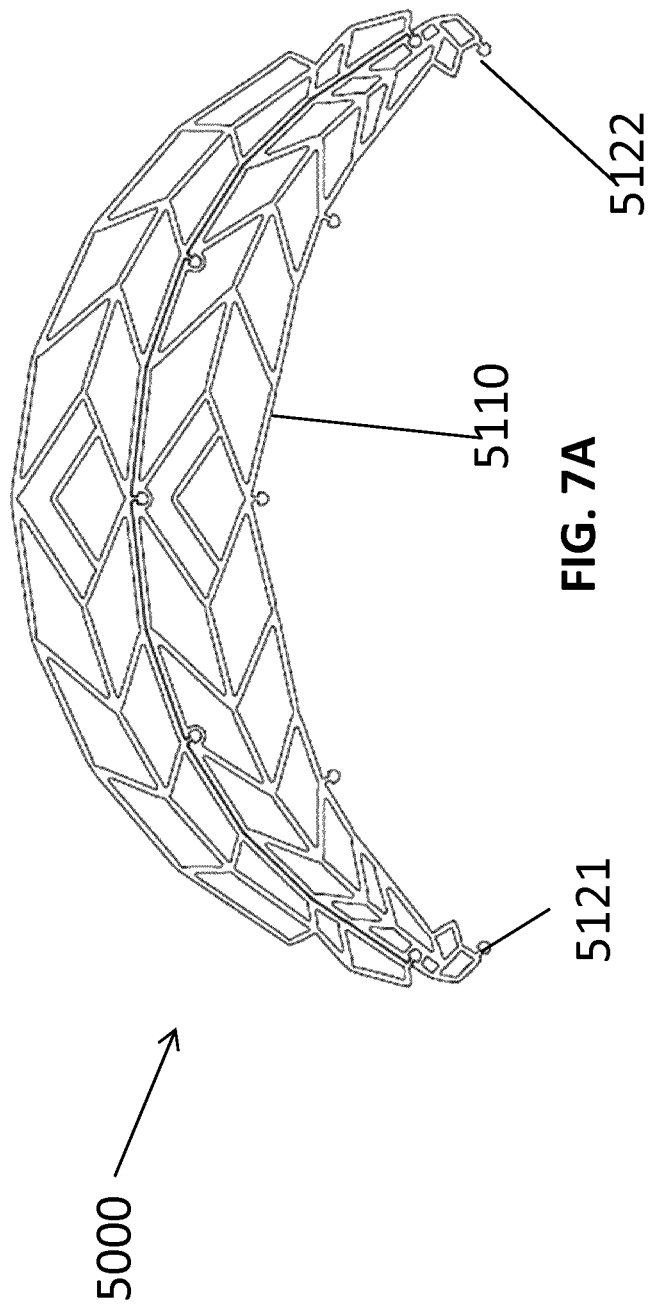
Figure 7C:
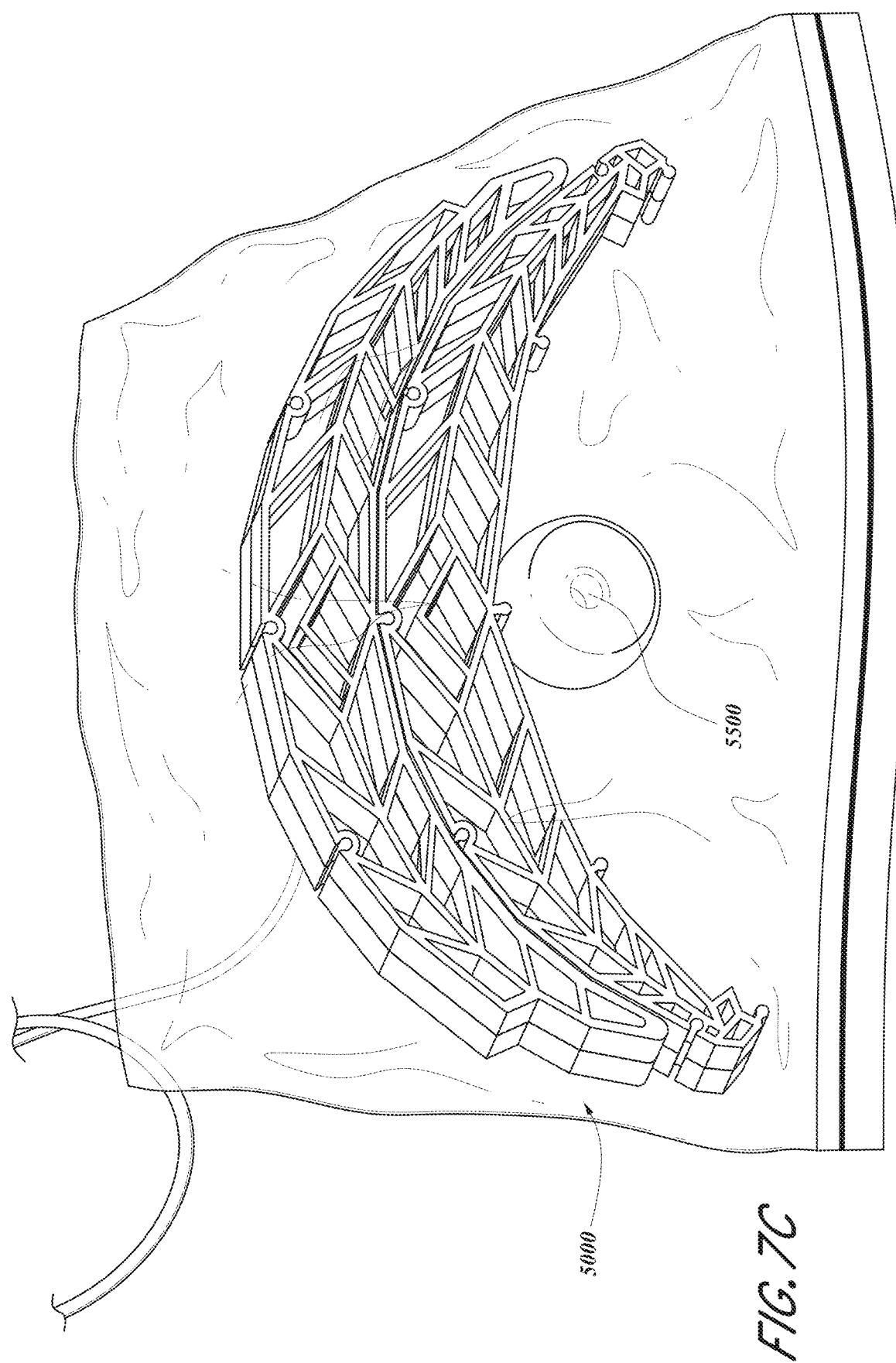
Figure 7D:
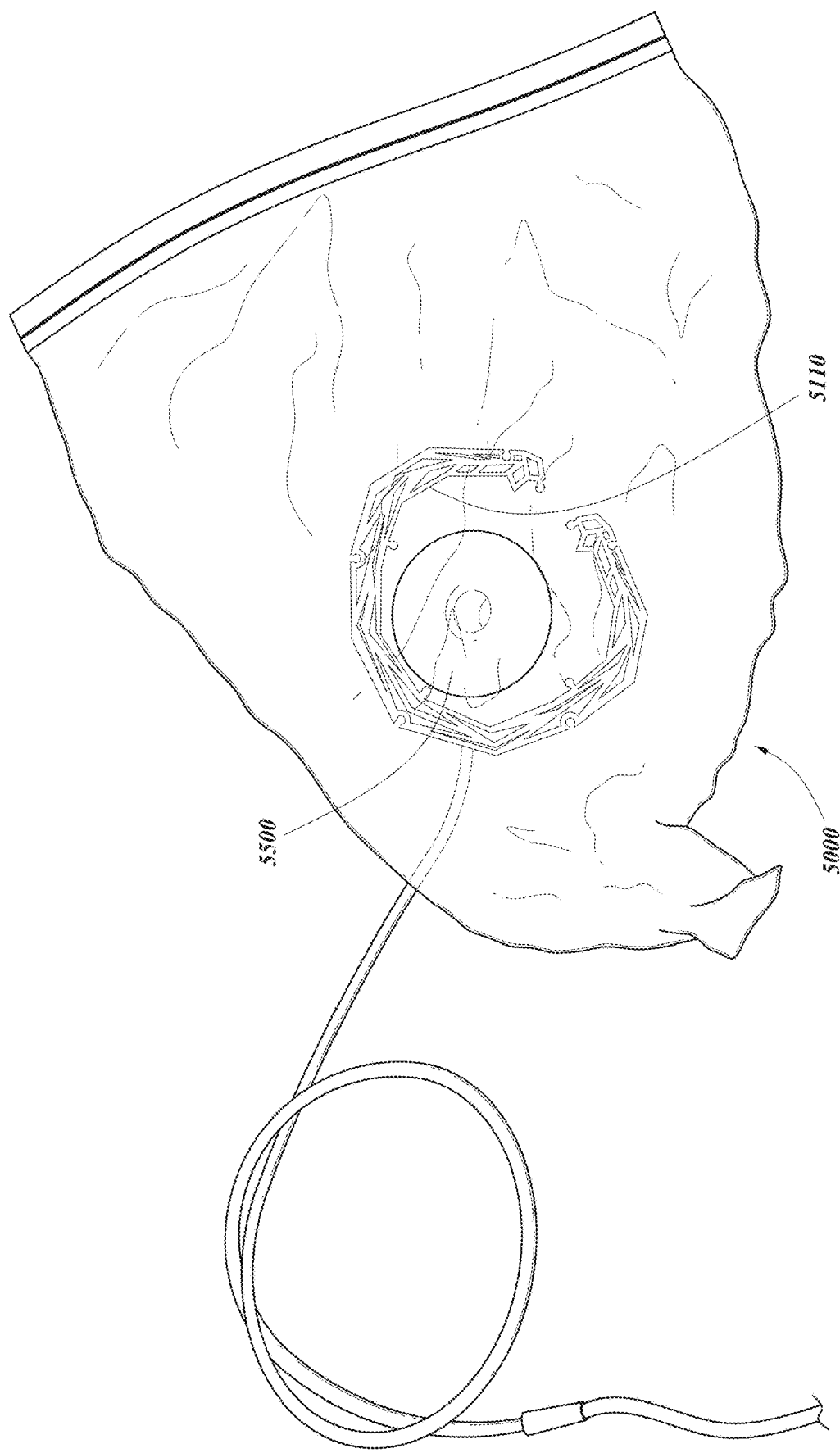

FIGS. 6A-7B compares the clamping of an embodiment of the clamping structure 5000 and the inner segment 5100 without the detachable segment 5200. Before collapse, the curvature of the concave side 5110 and the distance between the first end 5121 and the second end 5122 is identical as shown in FIGS. 6A and 7A. However, after collapse, the clamping structure with the detachable segment installed which is illustrated in FIG. 7B shows greater degree of transformation than the clamping structure without detachable segment which is illustrated in FIG. 6B. Photographs of such embodiment are shown in FIGS. 7C-D. Here, an embodiment of object 5500 subject to clamping of 5000 is shown. Here, the concave side 5110 of the clamping structure 5000 in FIG. 7D would form a relatively more intimate contact with the contoured object with 5500 than the collapsed clamping structure 5100 of FIG. 6B would have formed. Therefore, where such proper fit of curvature between the concave side and contoured object is desired, the control of curvature by installing and removing detachable segments may be useful. In some embodiments, the clamping structure may show gradually greater clamping activity as one, two, three and more detachable segments are installed, so that the user of the clamping structure may adjust the degree of clamping activity by removing or installing the detachable structure. In other embodiments, the clamping structure may be designed to clamp in smaller degree with the detachable segments installed.

FIGS. 8A-E: Stackable Clamping Device

Figure 8A:
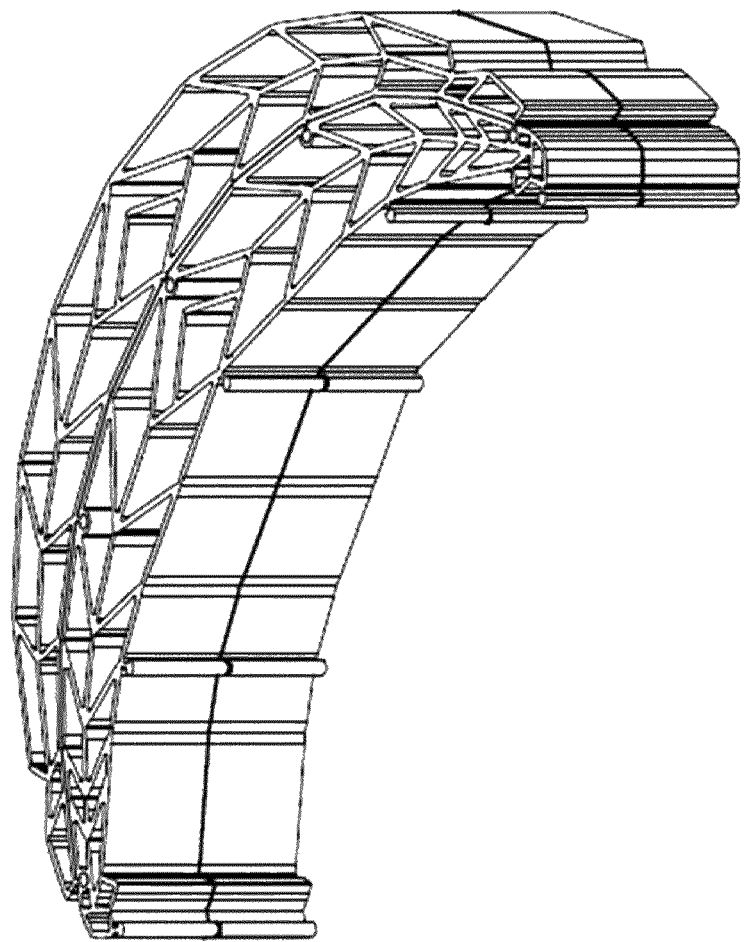
FIGS. 8A-B illustrate a perspective view and an exploded view of an embodiment of stacked clamping structures.
Figure 8B:
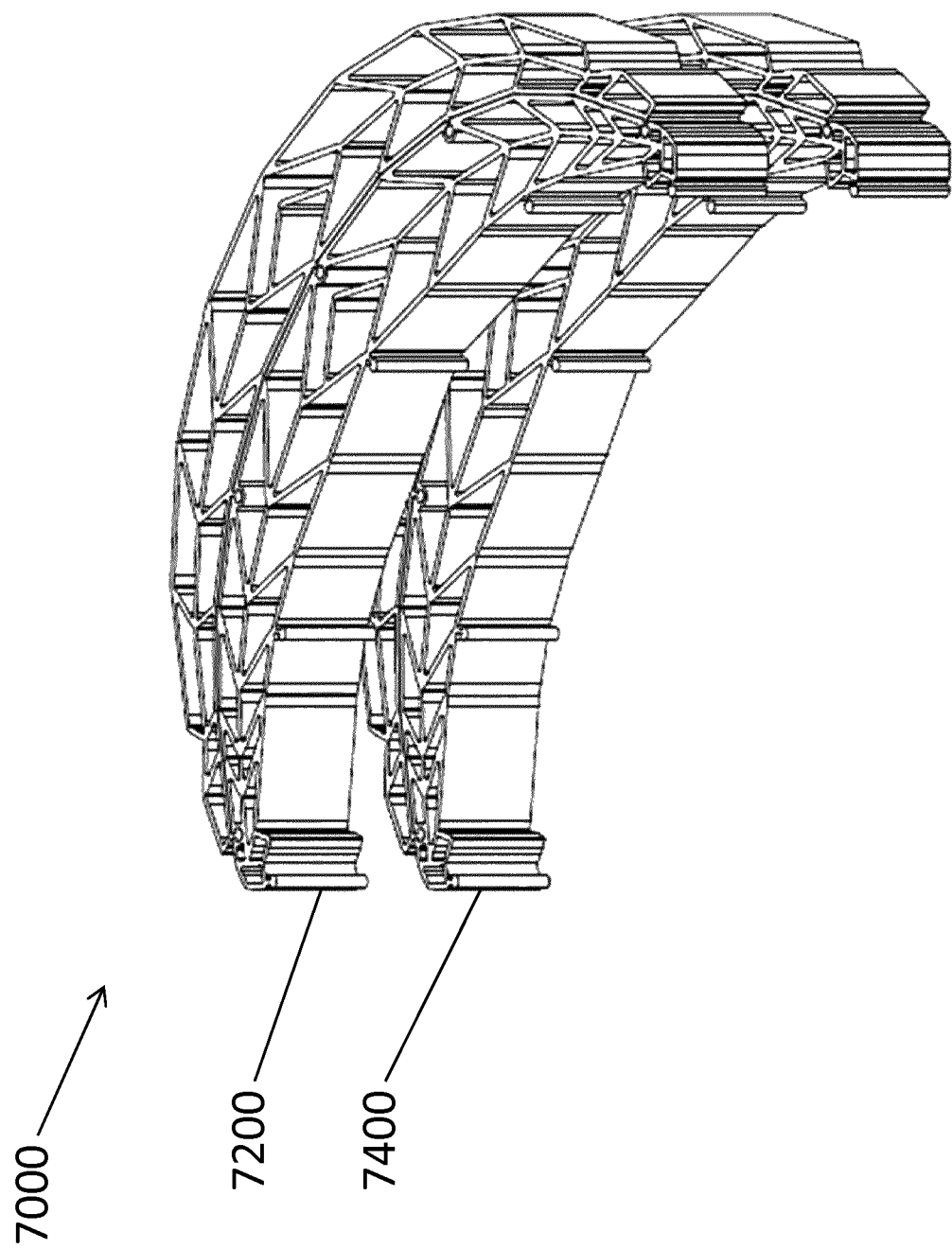

FIG. 8A depicts an embodiment of a clamping device 7000, comprising 7200 and 7400, similar to those disclosed elsewhere in the specification, such as in relation to FIGS. 2A-7D. However, here, the clamping structures 7200 and 7400 may be stacked one atop the other to provide a clamping device 7000 with greater height. With greater height, the stacked clamping device will have wider side walls and may be applied to a larger object. FIG. 8B illustrates an exploded view of such embodiments. In some embodiments, the clamping device may comprise two stackable clamping structures, three stackable clamping structures, four stackable clamping structures, five stackable clamping structures, or more than five stackable clamping structures. In some embodiments, all stackable clamping structures have the same size. In other embodiments, stackable clamping structures have different sizes. Similar to the detachable segments described above, the stackable clamping structures may be packaged separately as kits. In some embodiments, the stackable clamping structures contain attachment elements and/or receiving elements, such as those disclosed herein this section or elsewhere in the specification, allowing the stackable clamping structures to be attached to one another. In some embodiments, the stacked clamping device has similar collapsing behavior to that of individual clamping devices.

Figure 8C:
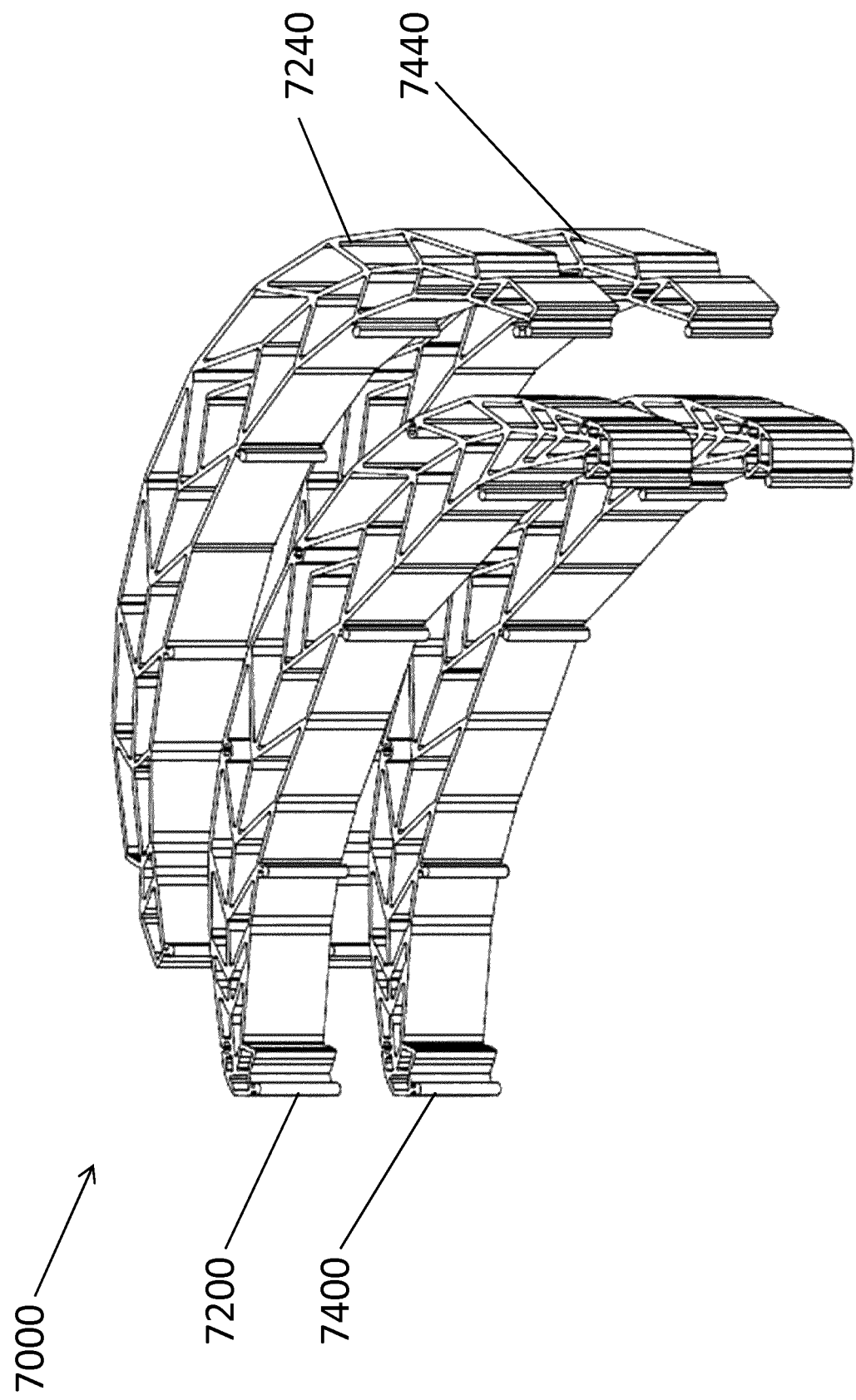
FIG. 8C illustrates an exploded view of an embodiment of stacked clamping structures.
Figure 8E:
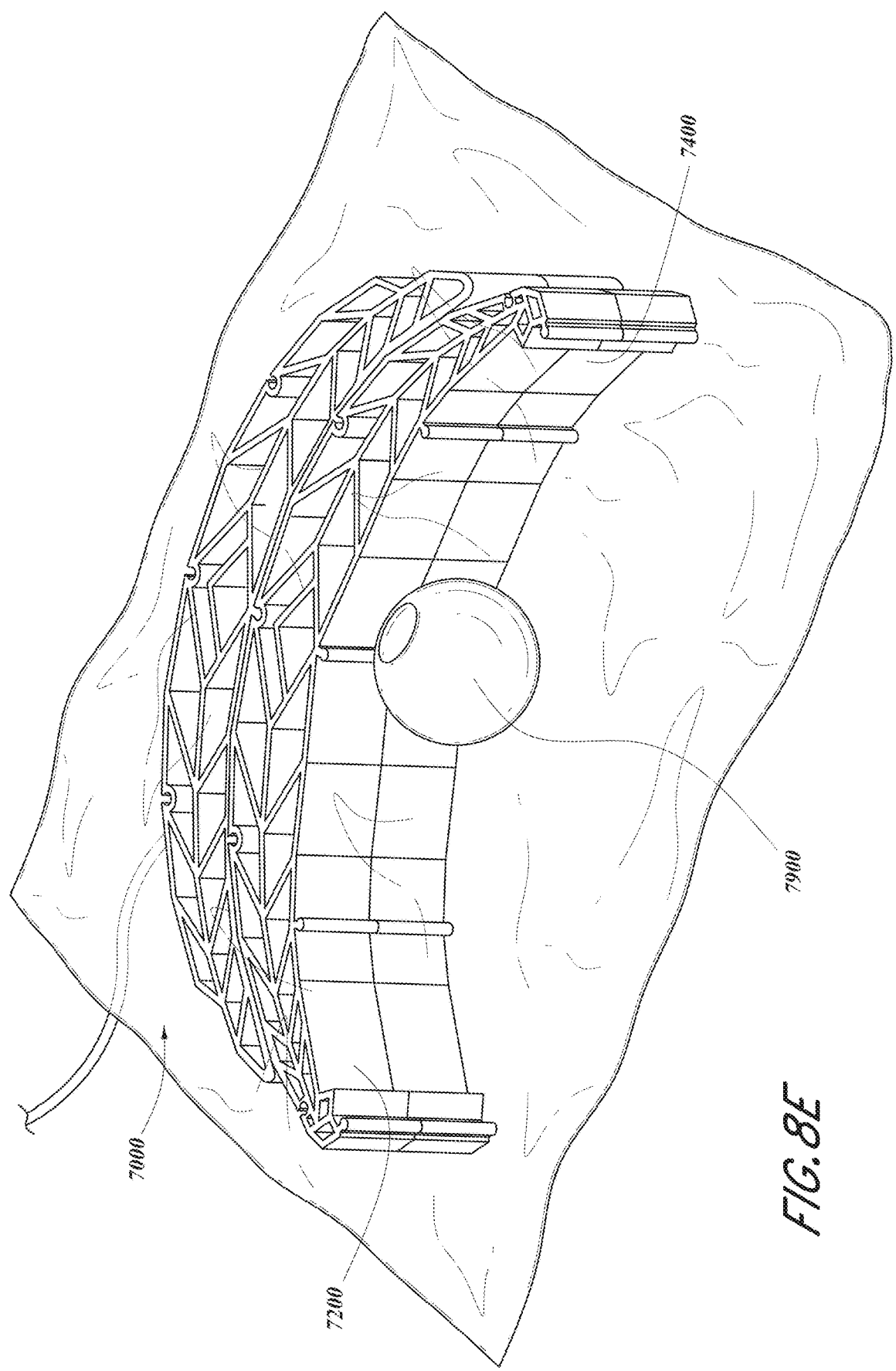

In some embodiments, as shown in FIG. 8C, stackable clamping structures may further comprise detachable elements 7240 and 7440, so that user can adjust both width and height of the clamping device. As described above in relation to FIGS. 6A-B and 7A-B, in some embodiments, adjusting the width by installing or removing the detachable elements may affect the collapsing behavior of the clamping structure. FIGS. 8D and 8E are photographs of an embodiment of stackable clamping structures 7000 which is similar with the stackable clamping structures described in relation to FIGS. 8A-8C and applied around a spherical object 7900.

Figure 9A:
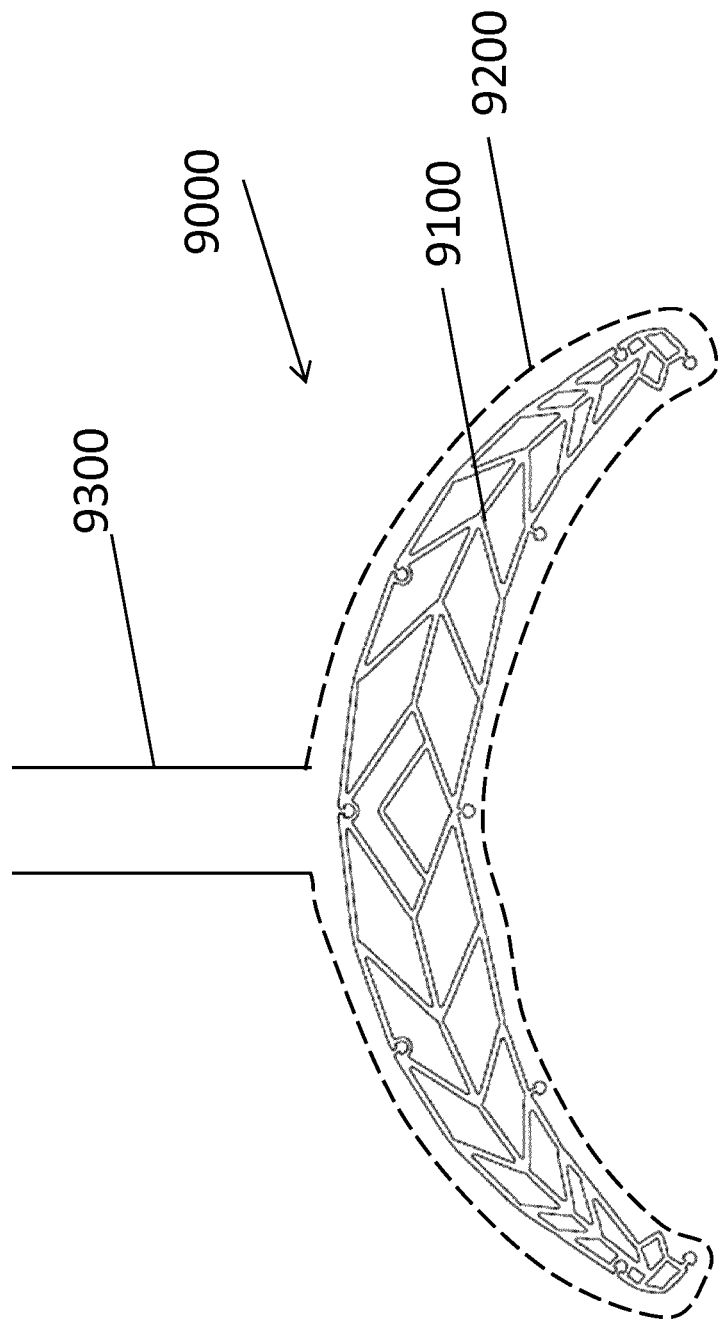
FIGS. 9A-B illustrate schematic views of embodiments of a pincer device having a clamping structure.
Figure 9B:
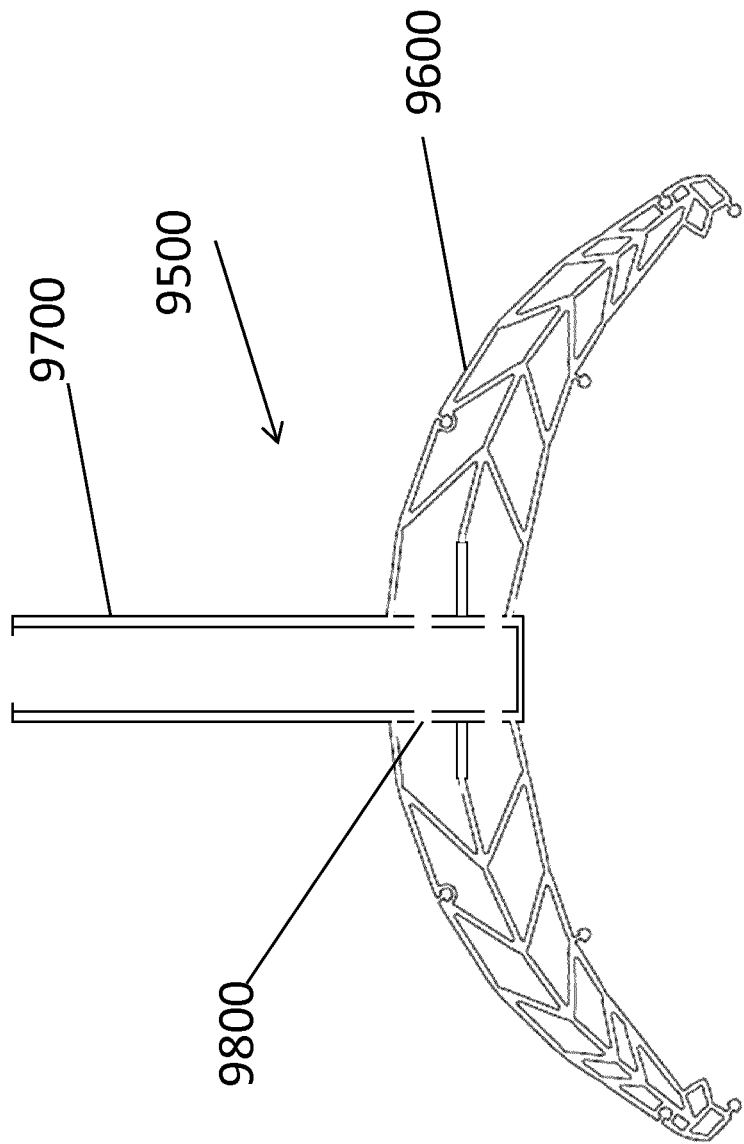

FIGS. 9A-9B: Pincer Device Having a Clamping Structure

As described elsewhere in the specification, clamping structures or clamping devices may be utilized for tools such as powered pincers or tweezers. FIGS. 9A-B illustrate schematic view of an embodiment of a pincer having a clamping structure. In FIG. 9A, a pincer 9000 contains a clamping structure 9100, a flexible membrane 9200 and a tube 9300. The clamping structure 9100 may be identical or similar with any clamping structures described in relation with FIGS. 2A-8E or elsewhere in the specification. For example, in some embodiments, the clamping structure 9100 may have a fluid path or notches (not shows) between cells, such that negative pressure can propagate through the fluid path or notches.

The tube 9300 may be configured to deliver negative pressure to the clamping structure 9100. The tube 9300 may be fluidically connected with a source of negative pressure, and in some embodiments, the source of negative pressure may be integrated or mounted on the tube 9300. In some embodiments, the pincer 9000 may have additional conduits to deliver negative pressure to the clamping structure 9100. The tube 9300 may be constructed from relatively rigid material and maintain its structure, so that the tube 9300 may be utilized as a grip or stick which the user of the pincer can hold.

The flexible membrane 9200 may cover the clamping structure 9100 and form a fluid-tight seal with the tube 9300. In some embodiments, the membrane 9200 may include a port, such that the tube 9300 can be connected with the membrane 9200. The flexible membrane 9200 may be constructed from a flexible film material or any other suitable materials. In some embodiments, the flexible membrane 9200 may only cover the top end and the bottom end of the cells, forming a fluid tight seal with the clamping structure.

FIG. 9B illustrates another embodiment of a pincer 9500. The pincer 9500 may be similar with the pincer 9000 of FIG. 9A. However here, the pincer 9500 may contain a tube 9700 directly integrated with a clamping structure 9600. The tube 9700 may have one or more air holes 9800 which is configured to fluidically connect the tube 9700 with one or more cells of 9600. In some embodiments, the clamping structure 9600 may have a fluid path or notches (not shows) between cells, such that negative pressure can further propagate through the fluid path or notches.

In some embodiments, the tube 9700 and the clamping structure 9600 could be constructed as a single piece. The pincer 9500 may further include a flexible membrane which encases the clamping structure and form a fluid tight seal around the clamping structure 9600. In some embodiments, the flexible membrane may only cover the top end and the bottom end of each cells, forming fluid tight seal with the clamping structure.

Even though clamping structures shown in FIGS. 2A-8D are single-curved structures which will increase their curvature upon collapse under negative pressure, different designs and further applications of these embodiments are also possible. For example, a straight-line shaped collapsible structure having similar cell configuration with clamping structures described in relation with FIGS. 2A-8D may bend along its length upon application of negative pressure. Compound shapes may also be provided by combining multiple collapsible structures similar with clamping structures described in relation with FIGS. 2A-8D together in different orientations. The collapsible structure may be enclosed within a cover member to form an enclosed, airtight space. Application of negative pressure to the enclosed space can cause the collapsible structure to collapse from the initial shape to the collapsed shape. In some embodiments, a more complex structure may constructed from more rigid parts (e.g., beams, skeletons) and collapsible structures similar with clamping structures described in relation with FIGS. 2A-8D which connect and act as joints of more rigid parts, such that the overall shape of the structure transforms in predetermined fashion upon application of negative pressure.

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombinations. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A collapsible structure for use with negative pressure, the collapsible structure comprising:
   a plurality of strips extending a length of the collapsible structure between a first end of the collapsible structure and a second end of the collapsible structure, the plurality of strips comprising a first strip, the first strip curved concavely along a horizontal plane relative to a longitudinal axis of the collapsible structure;
a plurality of intervening members, each intervening member of the plurality of intervening members connecting two respective strips of the plurality of strips, at least one of intervening member of the plurality of intervening members configured to adjust upon application of negative pressure to facilitate collapse of the collapsible structure; and
a plurality of cells at least partially formed by at least one of the plurality of strips or the plurality of intervening members, the plurality of cells provided along the horizontal plane parallel to the length of the collapsible structure and to a width of the collapsible structure, each cell of the plurality of cells comprising an opening extending through the cell in a direction perpendicular to the horizontal plane,
wherein the collapsible structure is configured to contract along the horizontal plane upon application of negative pressure to the collapsible structure such that the first end of the collapsible structure and the second end of the collapsible structure approach a central transverse axis extending along the width.

2. The collapsible structure of claim 1, wherein a second strip of the plurality of strips is curved convexly along the horizontal plane relative to the longitudinal axis of the collapsible structure.

3. The collapsible structure of claim 2, wherein the first strip at least partially defines a first sidewall of the collapsible structure, and wherein the second strip at least partially defines a second sidewall of the collapsible structure.

4. The collapsible structure of claim 3, wherein the first sidewall and the second sidewall each tapers toward the first end and the second end.

5. The collapsible structure of claim 1, further comprising at least one detachable segment.

6. The collapsible structure of claim 5, wherein the at least one detachable segment comprises at least one attachment element.

7. The collapsible structure of claim 1, wherein the collapsible structure is at least partially crescent-shaped.

8. The collapsible structure of claim 1, wherein the collapsible structure is configured to increase curvature along the horizontal plane upon the collapse of the plurality of cells such that the first end and the second end approach the central transverse axis and apply a clamping force.

9. The collapsible structure of claim 1, wherein the collapsible structure is configured to collapse along a horizontal plane parallel to the length of the collapsible structure and to a width of the collapsible structure such that the first end and the second end approach one another.

10. The collapsible structure of claim 1, wherein the collapsible structure is configured to grip or clamp around objects under negative pressure.

11. An apparatus comprising:
the collapsible structure of claim 1; and
a source of negative pressure.

12. The apparatus of claim 11, further comprising a port configured to transmit negative pressure through a drape when the drape is placed over the collapsible structure.

13. A collapsible structure for use with negative pressure, the collapsible structure comprising:
a plurality of strips extending a length of the collapsible structure between a first end of the collapsible structure and a second end of the collapsible structure;
a plurality of intervening members, each intervening member of the plurality of intervening members connecting two respective strips of the plurality of strips, at least one of intervening member of the plurality of intervening members configured to adjust upon application of negative pressure to facilitate collapse of the collapsible structure;
a plurality of cells at least partially formed by at least one of the plurality of strips or the plurality of intervening members, the plurality of cells provided along a horizontal plane parallel to the length of the collapsible structure and to a width of the collapsible structure, each cell of the plurality of cells comprising an opening extending through the cell in a direction perpendicular to the horizontal plane;
wherein the collapsible structure is configured to contract along the horizontal plane upon application of negative pressure to the collapsible structure such that the first end of the collapsible structure and the second end of the collapsible structure approach a central transverse axis extending along the width; and
wherein a length of cells adjacent to the first end or the second end of the collapsible structure is less than a length of cells adjacent to the central transverse axis.

14. A method of gripping one or more objects, the method comprising:
providing a collapsible structure comprising a plurality of cells provided along a horizontal plane parallel to a length of the collapsible structure and to a width of the collapsible structure, each cell of the plurality of cells comprising an opening extending through the cell in a direction perpendicular to the horizontal plane, wherein the collapsible structure comprising;
a plurality of strips extending the length of the collapsible structure between a first end and a second end, and
a plurality of intervening members, each intervening member of the plurality of intervening members connecting two respective strips of the plurality of strips, wherein the plurality of cells are at least partially formed by at least one of the plurality of strips or the plurality of intervening members;
positioning the collapsible structure adjacent to an object; and
contracting the collapsible structure along the horizontal plane of the collapsible structure to cause the collapsible structure to grip the object by applying negative pressure to the collapsible structure, wherein contracting the collapsible structure causes a first end of the collapsible structure and a second end of the collapsible structure to approach a central transverse axis of the collapsible structure extending along the width of the collapsible structure.

15. The method of claim 14, further comprising covering the collapsible structure with a drape.

16. The method of claim 15, wherein contracting the collapsible structure comprises applying negative pressure to the collapsible structure through the drape via a port.

17. The method of claim 14, further comprising establishing fluid communication between the collapsible structure and a source of negative pressure.

18. The method of claim 14, wherein positioning the collapsible structure adjacent to the object comprises positioning the object adjacent to a first sidewall of the collapsible structure, and wherein the first sidewall is curved concavely along the horizontal plane relative to a longitudinal axis of the collapsible structure.

19. A collapsible structure for use with negative pressure, the collapsible structure comprising:

a plurality of strips extending a length of the collapsible structure between a first end of the collapsible structure and a second end of the collapsible structure;

a plurality of intervening members, each intervening member of the plurality of intervening members connecting two respective strips of the plurality of strips, at least one of intervening member of the plurality of intervening members configured to adjust upon application of negative pressure to facilitate collapse of the collapsible structure;

a plurality of cells at least partially formed by at least one of the plurality of strips or the plurality of intervening members, the plurality of cells provided along a horizontal plane parallel to the length of the collapsible structure and to a width of the collapsible structure, each cell of the plurality of cells comprising an opening extending through the cell in a direction perpendicular to the horizontal plane;

wherein the collapsible structure is configured to contract along the horizontal plane upon application of negative pressure to the collapsible structure such that the first end of the collapsible structure and the second end of the collapsible structure approach a central transverse axis extending along the width; and wherein the collapsible structure is at least one of:

at least partially crescent-shaped, configured to increase curvature along the horizontal plane upon the collapse of the plurality of cells such that the first end and the second end approach the central transverse axis and apply a clamping force, or configured to collapse along a horizontal plane parallel to the length of the collapsible structure and to a width of the collapsible structure such that the first end and the second end approach one another.

20. The collapsible structure of claim 19, wherein the collapsible structure is at least partially crescent-shaped.

21. The collapsible structure of claim 19, wherein the collapsible structure is configured to increase curvature along the horizontal plane upon the collapse of the plurality of cells such that the first end and the second end approach the central transverse axis and apply a clamping force.

22. The collapsible structure of claim 19, wherein the collapsible structure is configured to collapse along a horizontal plane parallel to the length of the collapsible structure and to a width of the collapsible structure such that the first end and the second end approach one another.

* * * * *